US009668980B2

(12) United States Patent
DeRosa et al.

(10) Patent No.: US 9,668,980 B2
(45) Date of Patent: Jun. 6, 2017

(54) ENCAPSULATION OF MESSENGER RNA

(71) Applicant: RaNA Therapeutics, Inc., Lexington, MA (US)

(72) Inventors: Frank DeRosa, Lexington, MA (US); Shrirang Karve, Lexington, MA (US); Michael Heartlein, Lexington, MA (US)

(73) Assignee: RaNA Therapeutics, Inc., Lexington, MA (US)

( * ) Notice: Subject to any disclaimer, the term of this patent is extended or adjusted under 35 U.S.C. 154(b) by 0 days.

(21) Appl. No.: 14/790,562

(22) Filed: Jul. 2, 2015

(65) Prior Publication Data

US 2016/0038432 A1 Feb. 11, 2016

Related U.S. Application Data

(60) Provisional application No. 62/020,163, filed on Jul. 2, 2014.

(51) Int. Cl.
*A61K 31/7105* (2006.01)
*A61K 9/50* (2006.01)
*A61K 9/127* (2006.01)
*A61K 31/713* (2006.01)

(52) U.S. Cl.
CPC .......... *A61K 9/5089* (2013.01); *A61K 9/1271* (2013.01); *A61K 9/1272* (2013.01); *A61K 9/1277* (2013.01); *A61K 9/5015* (2013.01); *A61K 31/713* (2013.01)

(58) Field of Classification Search
CPC . A61K 9/1271; A61K 9/1277; A61K 31/7105
USPC ............................ 424/450; 514/44; 536/23.1
See application file for complete search history.

(56) References Cited

U.S. PATENT DOCUMENTS

| | | | |
|---|---|---|---|
| 5,705,385 A | 1/1998 | Bally et al. | |
| 5,948,441 A * | 9/1999 | Lenk .................... | A61K 9/1277 264/4.1 |
| 5,976,567 A | 11/1999 | Wheeler | |
| 5,981,501 A | 11/1999 | Wheeler et al. | |
| 6,534,484 B1 | 3/2003 | Wheeler et al. | |
| 6,815,432 B2 | 11/2004 | Wheeler et al. | |
| 6,855,296 B1 * | 2/2005 | Baker .................... | A61K 9/1277 264/4 |
| 7,422,902 B1 | 9/2008 | Wheeler et al. | |
| 7,745,651 B2 | 6/2010 | Heyes et al. | |
| 7,799,565 B2 | 9/2010 | MacLachlan et al. | |
| 7,803,397 B2 | 9/2010 | Heyes et al. | |
| 7,901,708 B2 | 3/2011 | MacLachlan et al. | |
| 8,101,741 B2 | 1/2012 | Maclachlan et al. | |
| 8,188,263 B2 | 5/2012 | Maclachlan et al. | |
| 8,236,943 B2 | 8/2012 | Lee et al. | |
| 8,329,070 B2 | 12/2012 | MacLachlan et al. | |
| 8,513,403 B2 | 8/2013 | MacLachlan et al. | |
| 8,569,256 B2 | 10/2013 | Heyes et al. | |
| 8,710,200 B2 | 4/2014 | Schrum et al. | |
| 8,822,663 B2 | 9/2014 | Schrum et al. | |
| 8,853,377 B2 | 10/2014 | Guild et al. | |
| 8,883,202 B2 | 11/2014 | Manoharan et al. | |
| 8,936,942 B2 | 1/2015 | Heyes et al. | |
| 8,980,864 B2 | 3/2015 | Hoge et al. | |
| 8,999,351 B2 | 4/2015 | Manoharan et al. | |
| 8,999,950 B2 | 4/2015 | MacLachlan et al. | |
| 9,018,187 B2 | 4/2015 | Heyes et al. | |
| 9,051,567 B2 | 6/2015 | Fitzgerald et al. | |
| 9,061,059 B2 | 6/2015 | Chakraborty et al. | |
| 9,074,208 B2 | 7/2015 | MacLachlan et al. | |
| 9,089,604 B2 | 7/2015 | Chakraborty et al. | |
| 9,095,552 B2 | 8/2015 | Chakraborty et al. | |
| 9,107,886 B2 | 8/2015 | Chakraborty et al. | |
| 9,114,113 B2 | 8/2015 | Chakraborty et al. | |
| 9,181,319 B2 | 11/2015 | Schrum et al. | |
| 9,186,325 B2 | 11/2015 | Manoharan et al. | |
| 9,186,372 B2 | 11/2015 | de Fougerolles et al. | |
| 9,187,748 B2 | 11/2015 | Geisbert et al. | |
| 9,192,651 B2 | 11/2015 | Chakraborty et al. | |
| 9,220,755 B2 | 12/2015 | Chakraborty et al. | |
| 9,220,792 B2 | 12/2015 | Chakraborty et al. | |
| 9,233,141 B2 | 1/2016 | Chakraborty et al. | |
| 9,254,311 B2 | 2/2016 | Bancel et al. | |
| 9,295,689 B2 | 3/2016 | de Fougerolles et al. | |
| 9,301,993 B2 | 4/2016 | Chakraborty et al. | |
| 9,303,079 B2 | 4/2016 | Chakraborty et al. | |
| 9,334,328 B2 | 5/2016 | Schrum et al. | |
| 9,345,780 B2 | 5/2016 | Manoharan et al. | |
| 9,352,042 B2 | 5/2016 | Heyes et al. | |
| 9,352,048 B2 | 5/2016 | Manoharan et al. | |
| 9,364,435 B2 | 6/2016 | Yaworski et al. | |
| 2002/0192651 A1 | 12/2002 | Wheeler et al. | |
| 2003/0181410 A1 | 9/2003 | Wheeler et al. | |
| 2004/0142025 A1 * | 7/2004 | MacLachlan .......... | A61K 9/127 424/450 |
| 2006/0008910 A1 | 1/2006 | MacLachlan et al. | |
| 2006/0083780 A1 | 4/2006 | Heyes et al. | |
| 2007/0135372 A1 | 6/2007 | MacLachlan et al. | |
| 2009/0270481 A1 | 10/2009 | MacLachlan et al. | |
| 2010/0041152 A1 | 2/2010 | Wheeler et al. | |
| 2010/0323356 A1 | 12/2010 | Inoue et al. | |
| 2011/0244026 A1 | 10/2011 | Guild et al. | |
| 2011/0256175 A1 | 10/2011 | Hope et al. | |
| 2011/0311583 A1 | 12/2011 | Manoharan et al. | |
| 2012/0065252 A1 | 3/2012 | Schrum et al. | |
| 2012/0128760 A1 | 5/2012 | Manoharan et al. | |
| 2012/0142756 A1 | 6/2012 | Guild et al. | |
| 2012/0202871 A1 | 8/2012 | Heyes et al. | |
| 2012/0237975 A1 | 9/2012 | Schrum et al. | |

(Continued)

FOREIGN PATENT DOCUMENTS

| | | |
|---|---|---|
| CA | 2807 552 | 9/2012 |
| EP | 1519 714 | 10/2010 |

(Continued)

*Primary Examiner* — Kevin Hill
(74) *Attorney, Agent, or Firm* — Fangli Chen; Proskauer Rose LLP

(57) ABSTRACT

The present invention provides an improved process for lipid nanoparticle formulation and mRNA encapsulation. In some embodiments, the present invention provides a process of encapsulating messenger RNA (mRNA) in lipid nanoparticles comprising a step of mixing a mRNA solution and a lipid solution, wherein the mRNA solution and/or the lipid solution are at a pre-determined temperature greater than ambient temperature.

16 Claims, 5 Drawing Sheets

(56) References Cited

U.S. PATENT DOCUMENTS

| | | |
|---|---|---|
| 2012/0251618 A1 | 10/2012 | Schrum et al. |
| 2012/0328668 A1 | 12/2012 | Maclachlan et al. |
| 2013/0017223 A1 | 1/2013 | Hope et al. |
| 2013/0195967 A1 | 8/2013 | Guild et al. |
| 2013/0237594 A1 | 9/2013 | De Fougerolles et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2014/0010861 A1 | 1/2014 | Bancel et al. |
| 2014/0044772 A1 | 2/2014 | MacLachlan et al. |
| 2014/0105964 A1 | 4/2014 | Bancel et al. |
| 2014/0105965 A1 | 4/2014 | Bancel et al. |
| 2014/0147432 A1 | 5/2014 | Bancel et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0171485 A1 | 6/2014 | Bancel et al. |
| 2014/0179756 A1 | 6/2014 | MacLachlan et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0194494 A1 | 7/2014 | Bancel et al. |
| 2014/0199371 A1 | 7/2014 | Bancel et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0221465 A1 | 8/2014 | Bancel et al. |
| 2014/0243399 A1 | 8/2014 | Schrum et al. |
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0275227 A1 | 9/2014 | Hoge et al. |
| 2014/0275229 A1 | 9/2014 | Bancel et al. |
| 2014/0294937 A1 | 10/2014 | MacLachlan et al. |
| 2014/0343129 A1 | 11/2014 | de Fougerolles et al. |
| 2015/0005372 A1 | 1/2015 | Hoge et al. |
| 2015/0017211 A1 | 1/2015 | de Fougerolles et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0064725 A1 | 3/2015 | Schrum et al. |
| 2015/0086614 A1 | 3/2015 | Bancel et al. |
| 2015/0111248 A1 | 4/2015 | Bancel et al. |
| 2015/0111945 A1 | 4/2015 | Geisbert et al. |
| 2015/0166465 A1 | 6/2015 | Chen et al. |
| 2015/0190515 A1 | 7/2015 | Manoharan et al. |
| 2015/0265708 A1 | 9/2015 | Manoharan et al. |
| 2015/0315541 A1 | 11/2015 | Bancel et al. |
| 2015/0315584 A1 | 11/2015 | MacDonald et al. |
| 2015/0366997 A1 | 12/2015 | Guild et al. |
| 2016/0095924 A1 | 4/2016 | Hope et al. |
| 2016/0114011 A1 | 4/2016 | Bancel et al. |
| 2016/0115477 A1 | 4/2016 | MacLachlan et al. |
| 2016/0115483 A1 | 4/2016 | MacLachlan et al. |
| 2016/0136236 A1 | 5/2016 | Hoge et al. |
| 2016/0151284 A1 | 6/2016 | Heyes et al. |
| 2016/0158385 A1 | 6/2016 | Bancel et al. |
| 2016/0193299 A1 | 7/2016 | De Fougerolles et al. |
| 2016/0194368 A1 | 7/2016 | Hoge et al. |
| 2016/0194625 A1 | 7/2016 | Hoge et al. |
| 2016/0213785 A1 | 7/2016 | Manoharan et al. |
| 2016/0237108 A1 | 8/2016 | Fraley et al. |
| 2016/0237134 A1 | 8/2016 | Hoge et al. |

FOREIGN PATENT DOCUMENTS

| | | | |
|---|---|---|---|
| EP | 2449 106 | | 5/2012 |
| EP | 2338 478 | | 6/2013 |
| EP | 2823 809 | | 1/2015 |
| WO | WO2005/026372 | | 3/2005 |
| WO | WO2005/121348 | | 12/2005 |
| WO | WO2009/127060 | | 10/2009 |
| WO | WO2010/042877 | | 4/2010 |
| WO | WO 2011/068810 | * | 6/2011 |
| WO | WO2011/141705 | | 11/2011 |
| WO | WO2012/019168 | | 2/2012 |
| WO | WO2012/135805 | | 10/2012 |
| WO | WO2012/170930 | | 12/2012 |
| WO | WO2013/039857 | | 3/2013 |
| WO | WO2013/039861 | | 3/2013 |
| WO | WO2013/090186 | | 6/2013 |
| WO | WO2013/101690 | | 7/2013 |
| WO | WO2013/126803 | | 8/2013 |
| WO | WO2013/130161 | | 9/2013 |
| WO | WO2013/151663 | | 10/2013 |
| WO | WO2013/151664 | | 10/2013 |
| WO | WO2013/151666 | | 10/2013 |
| WO | WO2013/151667 | | 10/2013 |
| WO | WO2013/151668 | | 10/2013 |
| WO | WO2013/151670 | | 10/2013 |
| WO | WO2013/151671 | | 10/2013 |
| WO | WO2013/151672 | | 10/2013 |
| WO | WO2013/151736 | | 10/2013 |
| WO | WO2014/089486 | | 7/2014 |
| WO | WO2014/113089 | | 7/2014 |
| WO | WO2014/144039 | | 9/2014 |
| WO | WO2014/144711 | | 9/2014 |
| WO | WO2014/144767 | | 9/2014 |
| WO | WO2014/152027 | | 9/2014 |
| WO | WO2014/152030 | | 9/2014 |
| WO | WO2014/152031 | | 9/2014 |
| WO | WO2014/152211 | | 9/2014 |
| WO | WO2014/152540 | | 9/2014 |
| WO | WO2014/158795 | | 10/2014 |
| WO | WO2014/159813 | | 10/2014 |
| WO | WO2015/006747 | | 1/2015 |
| WO | WO2015/048744 | | 4/2015 |
| WO | WO2015/051169 | | 4/2015 |
| WO | WO2015/051173 | | 4/2015 |
| WO | WO2015/058069 | | 4/2015 |
| WO | WO2015/011633 | | 1/2016 |
| WO | WO2016/054421 | | 4/2016 |
| WO | WO2016/071857 | | 5/2016 |
| WO | WO2016/077123 | | 5/2016 |
| WO | WO2016/077125 | | 5/2016 |
| WO | WO2016/118724 | | 7/2016 |
| WO | WO2016/118725 | | 7/2016 |

* cited by examiner

Figure 1. Scaled-Up Formulation Process with Homogenous Flow Pumps

Figure 2. Scaled-Up Formulation Process with Homogenous Flow Pumps

Figure 3. Scaled-Up Formulation Process with Homogenous Flow Pumps.

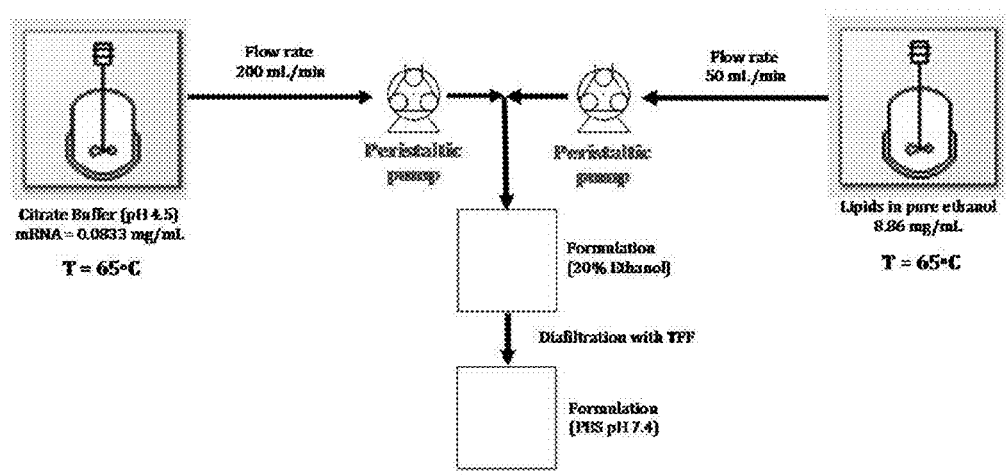
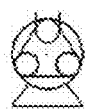
Figure 5 Scaled-Up Formulation Process with Peristaltic Pumps

SEQUENCE LISTING

<160> NUMBER OF SEQ ID NOS: 10

<210> SEQ ID NO 1
<211> LENGTH: 250
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: See specification as filed for detailed
      description of substitutions and preferred embodiments

<400> SEQUENCE: 1
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa                                                                                             250

<210> SEQ ID NO 2
<211> LENGTH: 1130
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 2
ggacagaucg ccuggagacg ccauccacgc uguuugacc uccauagaag acaccgggac            60
cgauccagcc uccgcggccg ggaacggugc auuggaacgc ggauucccg ugccaagagu           120 gacucaccgu ccuugacacg auggccauga gcagcggagg cagcggcgga ggagugcccg          180
agcaggagga cagcgugcug uucaggagag gcaccggcca gagcgaugac agcgauaucu          240
gggacgauac cgcucugauc aaggccuacg acaaggccgu ggccagcuuc aagcacgccc          300
ugaaaaacgg cgacaucugc gagaccagcg gcaagcccaa gacaacccccc aagagaaagc        360 ccgccaagaa gaauaagagc cagaaaaaga acaccgccgc cagccugcag caguggaagg          420
ugggcgacaa gugcagcgcc aucuggagcg aggacggcug caucuaccccc gccaccaucg        480 ccagcaucga cuucaagaga gagaccugcg uggucgugua caccggcuac ggcaacagag          540
aggagcagaa ccugagcgac cugcugagcc cauuuguga gguggccaau aacaucgaac          600
agaacgccca ggagaacgag aaugaaagcc aggugagcac cgacgagagc gagaacagca         660
gaucuccugg caacaagagc gacaacauca agccuaaguc ugccccuugg aacagcuucc         720
ugcccccucc uccacccaug cccggaccca gacugggacc cggaaaaccu ggccugaagu         780
ucaacggacc accucccccu ccaccuccuc ccccaccuca ucccugagc ugcuggcugc           840 caccuucccc cagcggaccc ccuaucaucc caccaccccc ucccaucugc cccgacagcc         900
uggacgacgc cgaugcccug ggcagcaugc ugaucagcug guacaugagc ggcuaccaca         960
caggauacua caugggcuuc agacagaacc agaaggaggg cagaugcucc cacucccuga       1020
acugacgggu ggcaucccug ugaccccucc ccagugccuc uccuggcccu ggaaguugcc        1080
acuccagugc ccaccagccu uguccuaaua aaauuaaguu gcaucaagcu                    1130

<210> SEQ ID NO 3
<211> LENGTH: 1535
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 3
ggacagaucg ccuggagacg ccauccacgc uguuugacc uccauagaag acaccgggac            60
cgauccagcc uccgcggccg ggaacggugc auuggaacgc ggauucccg ugccaagagu           120 gacucaccgu ccuugacacg augcagcuga ggaacccaga acuacaucug ggcugcgcgc          180
uugcgcuucg cuuccuggcc cucguuuccu gggacauccc ugggggcuaga gcacuggaca        240 auggauuggc aaggacgccu accaugggcu ggcugcacug ggagcgcuuc augugcaacc          300
uugacugcca ggaagagcca gauuccugca ucagugagaa gcucuucaug gagauggcag         360
agcucauggu cucagaaggc uggaaggaug caggguauga guaccucugc auugaugacu         420
guuggauggc uccccaaaga gauucagaag gcagacuuca ggcagacccu cagcgcuuuc         480
cucaugggau ucgccagcua gcuaauuaug uucacagcaa aggacugaag cuagggauuu        540

```
augcagaugu uggaaauaaa accugcgcag gcuucccugg gaguuuugga uacuacgaca      600
uugaugccca gaccuuugcu gacugggag uagaucugcu aaaauuugau gguuguuacu      660
gugacaguuu ggaaaauuug gcagaugguu auaagcacau guccuuggcc cugaauagga      720
cuggcagaag cauuguguac uccgugagu ggcucuuua uauguggccc uuucaaaagc      780
ccaauuauac agaaauccga caguacugca aucacggcg aaauuugcu gacauugaug      840 auuccuggaa aaguauaaag aguaucuugg acuggacauc uuuuaaccag gagagaauug      900
uugauguugc uggaccaggg gguuggaaug acccagauau guuagugauu ggcaacuuug      960
gccucagcug gaaucagcaa guaacucaga uggcccucug ggcuaucaug gcugcuccuu    1020
uauucauguc uaaugaccuc cgacacauca gcccucaagc caaagcucuc cuucaggaua    1080
aggacguaau ugccaucaau caggaccccu ugggcaagca agguaccag cuugacagg      1140 gagacaacuu ugaagugugg gaacgaccuc ucucaggcuu agccugggcu uagcuauga    1200 uaaaccggca ggagauuggu ggaccucgcu cuuauaccau cgcaguugcu ucccugggua    1260
aaggagugcc cuguaauccu gccugcuuca ucacacagcu ccucccugug aaaaggaagc    1320 uagguucua ugaauggacu ucaagguuaa gaagucacau aaaucccaca ggcacuguuu    1380
ugcuucagcu agaaaauaca augcagaugu cauuaaaaga cuuacuuuaa cggguggcau    1440
cccugugacc cuccccagu gccucuccug gcccuggaag uugccacucc agugcccacc    1500
agccuugucc uaauaaaauu aaguugcauc aagcu                              1535
```

<210> SEQ ID NO 4
<211> LENGTH: 1484
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 4

```
ggacagaucg ccuggagacg ccauccacgc uguuugacc uccauagaag acaccgggac       60
cgauccagcc uccgcggccg ggaacggugc auuggaacgc ggauucccg ugccaagagu      120 gacucaccgu ccuugacacg augagcagca agggcagcgu ggugcuggcc uacagcggcg    180
gccuggacac cagcgcaluc cuggugucgg ugaaggagca gggcuacgac gugaucgccu    240
accuggccaa caucggccag aaggaggacu ucgaggaggc ccgcaagaag gcccugaagc    300
ugggcgccaa gaaggucuuc aucgaggacg ugagccgcga guucguggag gaguucaucu    360
ggcccgccau ccagagcagc gcccuguacg aggaccgcua ccugcggggc accagccugg    420 cccgcccucug caucgcccgc aagcagguigg agaucgccca gcgcgagggc gccaaguacg    480
ugagccacgg cgccaccggc aagggcaacg accaggugcg cuucgagcug agcugcuaca    540
gccuggcccc ccagaucaag gugaucgccc ccuggcgcau gcccgaguuc uacaaccgcu    600
ucaagggccg caacgaccug auggaguacg ccaagcagca cggcauccc auccccguga    660 cccccaagaa ccccuggagc auggacgaga accugaugca caucagcuac gaggccggca    720
uccuggagaa ccccaagaac caggcccccc ccggccugua caccaagacc caggaccccg    780
ccaaggcccc caacacccc gacauccugg agaucgaguu caagaagggc gugcccgdga    840
aggugaccaa cgugaaggac ggcaccaccc accagaccag ccuggagcug uucauguacc    900
ugaacgaggc ggccggcaag cacggcgcugg gccgcaucga caucguggag aaccgcuuca    960
ucggcaugaa gagccgcggc aucuacgaga ccccccgccgg caccauccug uaccacgccc   1020
```

```
accuggacau cgaggccuuc accauggacc gcgaggugcg caagaucaag cagggccugg    1080
gccugaaguu cgccgagcug guguacaccg gcuucuggca cagccccgag ugcgaguucg    1140
ugcgccacug caucgccaag agccaggagc gcguggaggg caaggugcag gugagcgugc    1200
ugaagggcca gguguacauc cugggccgcg agagccccu gagccuguac aacgaggagc     1260
uggugagcau gaacgugcag ggcgacuacg agcccaccga cgccaccggc uucaucaaca    1320
ucaacagccu cgccugaag gaguaccacc gccugcagag caaggugacc gccaagugac      1380
ggguggcauc ccugugaccc cuccccagug ccucuccugg cccuggaagu ugccacucca    1440
gugcccacca gccuuguccu aauaaaauua aguugcauca agcu                     1484
```

<210> SEQ ID NO 5
<211> LENGTH: 1898
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 5

```
ggacagaucg ccuggagacg ccauccacgc uguuuugacc uccauagaag acaccgggac      60
cgauccagcc uccgcggccg ggaacggugc auuggaacgc ggauccccg ugccaagagu      120 gacucaccgu ccuugacacg auggaagaug ccaaaaacau aagaagggc ccagcgccau      180 ucuacccacu cgaagacggg accgccggcg agcagcugca caaagccaug aagcgcuacg     240
cccuggugcc cggcaccauc gccuuuaccg acgcacauau cgagguggac auuaccuacg     300
ccgaguacuu cgagaugagc guucggcugg cagaagcuau gaagcgcuau gggcugaaua     360
caaaccaucg gaucguggug ugcagcgaga auagcuugca guucuucaug cccguguugg     420
gugcccuguu caucggugug gcuguggccc cagcuaacga caucuacaac gagcgcgagc     480
ugcugaacag caugggcauc agccagccca ccgucguauu cgugagcaag aaagggcugc     540
aaaagauccu caacgugcaa agaagcuac cgaucauaca aaagaucauc aucauggaua     600
gcaagaccga cuaccagggc uuccaaagca uguacaccuu cgugacuucc cauuugccac    660
ccggcuucaa cgaguacgac uucgugcccg agagcuucga ccgggacaaa accaucgccc    720
ugaucaugaa caguagugc aguaccggau gcccaagggg cguagcccua ccgcaccgca     780
ccgcuugugu ccgauucagu caugcccgcg accccaucuu cggcaaccag aucaucccg    840 acaccgcuau cccucagcgug gugccauuuc accacggcuu cggcauguuc accacgcugg    900
gcuacuugau cugcggcuuu cgggucgugc ucauguaccg cuucgaggag gagcuauucu    960
ugcgcagcuu gcaagacuau aagauucaau cugcccugcu ggugcccaca cuauuuagcu    1020
ucuucgcuaa gagcacucuc aucgacaagu acgaccuaag caacuugcac gagaucgcca    1080
gcggcggggc gccgcucagc aaggagguag gugaggccgu ggccaaacgc uuccaccuac    1140
caggcauccg ccagggcuac ggccugacag aaacaaccag cgccauucug aucaccccg    1200 aaggggacga caagccuggc gcaguaggca aggugugcc cuucuucgag gcuaaggugg    1260
uggacuugga caccgguaag acacgggug ugaaccagcg cggcgagcug ugcgucccgu    1320
gccccaugau caugagcggc uacguuaaca accccgaggc uacaaacgcu cucaucgaca    1380
aggacggcug gcugcacagc ggcgacaucg ccuacgggga cgaggacgag cacuucuuca    1440 ucgguggaccg gcugaagagc cugaucaaau acaaggcua ccaggucagcc ccagccgaac    1500 ugagagcau ccugcugcaa cacccccaaca ucuucgacgc cggggucgcc ggccugcccg    1560
```

```
acgacgaugc cggcgagcug cccgccgcag ucgucgugcu ggaacacggu aaaaccauga   1620
ccgagaagga gaucguggac uauguggcca gccagguuac aaccgccaag aagcugcgcg   1680
gugguguugu guucguggac gaggugccua aaggacugac cggcaaguug gacgcccgca   1740
agauccgcga gauucucauu aaggccaaga agggcggcaa gaucgccgug uaacggguggu   1800 caucccugug accccucccc agugccucuc cuggcccugg aaguugccac uccagugccc   1860
accagccuug uccaauaaaa auuaaguugc aucaagcu                           1898

<210> SEQ ID NO 6
<211> LENGTH: 1631
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 6
ggacagaucg ccuggagacg ccauccacgc uguuuugacc uccauagaag acaccgggac     60
cgauccagcc uccgcggccg ggaacggugc auuggaacgc ggauuccccg ugccaagagu    120
gacucaccgu ccuugacacg augcagcgcg ugaacaugau cauggcagaa ucaccaggcc    180
ucaucaccau cugccuuuua ggauaucuac ucagugcuga auguacaguu uuucuugauc    240
augaaaacgc aacaaaaauu cugaggcgga gaaggaggua uaauucaggu aaauuggaag    300
aguuuguuca agggaaccuu gagagagaau guaggaaga aagcuaguu uugaagaag       360 cacgagaagu uuugaaaac acugaaagaa caacugaauu uggaagcag auguugaug       420 gagaucagug ugaguccaau ccauguuuaa auggcggcag uugcaaggau gacauuaauu    480
ccuaugaaug uuggugcccc uuggauuug aaggaaagaa cugugaauua gaugugaacau    540 guaacauuaa gaauggcaga ugcgagcagu uuuguaaaaa uagugcugau aacaaggugg    600
uuugcuccug uacugaggga uaucgacuug cagaaaacca gaaguccugu gaaccagcag    660
ugccauuucc auguggaaga guucugcguu cacaaacuuc uaagcucacc cgugcugagg    720
cuguuuuucc ugaugugac uauguaaauu cuacgaagc ugaaaccauu uggauaaca      780 ucacucaaag caccccaauca uuuaaugacu ucacucgggu uguggugga aagaugcca    840 aaccagguca auucccuugg cagguguuu ugaaugguaa aguugaugca uucuguggag    900
gcucuaucgu uaaugaaaaa uggauuguaa cugcugccca cuguguugaa acuggguuua   960
aaauuacagu ugucgcaggu gaacauaaua uugaggagac agaacauaca gagcaaaagc   1020
gaaaugugau ucgaauuauu ccucaccaca acuacaaugc agcuauuaau aaguacaacc   1080
augacauugc ccuucggaa cuggacgaac ccuagugcu aaacagcuac guuacaccua   1140
uuugcauugc ugacaaggaa uacacgaaca ucuuccucaa auuggaucu ggcuauguaa   1200 gugcuggggg aagagucuuc cacaaaggga gaucagcuuu aguucuucag uaccuuagag   1260
uuccacuugu ugaccgagcc acaugucuuc gaucuacaaa guucaccauc uauaacaaca   1320
uguucugugc uggcuuccau gaaggaggua gagauucaug ucaaggagau agugggggac   1380
cccauguuac ugaagggaa gggaccaguu ucuuaacgg aauuauuagc uggggugaag   1440
agugugcaau gaaaggcaaa uauggaauau auaccaaggu aucccgguau gucaacugga   1500
uuaaggaaaa aacaaagcuc acuuaacggg uggcaucccu gugaccccuc ccagugccu    1560 cuccuggccc uggaaguugc cacuccagug cccaccagcc uuguccuaau aaaauuaagu   1620
ugcaucaagc u                                                        1631
```

<210> SEQ ID NO 7
<211> LENGTH: 1604
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 7

```
ggacagaucg ccuggagacg ccauccacgc uguuuugacc uccauagaag acaccgggac     60
cgauccagcc uccgcggccg ggaacggugc auuggaacgc ggauucccccg ugccaagagu    120
gacucaccgu ccuugacacg augagcaccg ccgugcugga aaccccggc cugggccgca      180
agcugagcga cuucggccag gagaccagcu acaucgagga caacugcaac agaacggcg      240
ccaucagccu gaucuucagc cugaaggagg agguggggcgc ccuggccaag gugcugcgcc    300
uguucgagga gaacgacgug aaccugaccc acaucgagag ccgccccagc cgccugaaga     360
aggacgagua cgaguucuuc acccaccugg acaagcgcag ccugcccgcc cugaccaaca     420
ucaucaagau ccugcgccac gacaucggcg ccaccgugca cgagcugagc cgcgacaaga     480
agaaggacac cgugcccugg uucccccgca ccauccagga gcuggaccgc uucgccaacc     540
agauccugag cuacggcgcc gagcuggacg ccgaccaccc cggcuucaag gaccccgugu     600
accgcgcccg ccgcaagcag uucgccgaca ucgccuacaa cuaccgccac ggccagccca     660
ucccccgcgu ggaguacaug gaggaggaga agaaccugg gggcaccgug uucaagaccc      720
ugaagagccu guacaagacc cacgccugcu acgaguacaa ccacaucuuc cccucugcugg    780
agaaguacug cggcuuccac gaggacaaca ucccccagcu ggaggacgug agccaguucc     840
ugcagaccug caccggcuuc cgccugcgcc ccguggccgg ccugcugagc agccgcgacu     900
uccugggcgg ccuggccuuc cgcguguucc acugcacccca guacauccgc cacggcagca     960
agcccaugua cacccccgag cccgacaucu gccacgagcu gcugggccac gugcccugu    1020
ucagcgaccg cagcuucgcc caguucagcc aggagaucgg ccuggccagc cugggcgccc  1080
ccgacgagua caucgagaag cuggccacca ucuacugguu caccgaugag uucgccugu   1140
gcaagcaggg cgacagcauc aaggccuacg cgccggccu gcugagcagc uucggcgagc    1200
ugcaguacug ccugagcgag aagcccaagc ugcugcccc ggagcuggag aagaccgcca    1260
uccagaacua caccgugacc gaguuccagc cccuguacua cguggccgag agcuucaacg    1320
acgccaagga gaaggucgc aacuucgccg ccaccaucc ccgcccccuuc agcgugcgcu    1380
acgaccccua cacccagcgc aucgaggugc uggacaacac cagcagcug aagauccugg    1440
ccgacagcau caacagcgag aucggcaucc ugucagcgc ccugcagaag aucaaguaac    1500
ggguggcauc ccugugaccc cucuccugg cccuggaagu ugccacucca               1560
gugcccacca gccuuguccu aauaaaauua aguugcauca agcu                      1604
```

<210> SEQ ID NO 8
<211> LENGTH: 4443
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 8

```
augcagcggu ccccgcucga aaaggccagu gucgugucca aacucuucuu cucauggacu    60
```

```
cggccuaucc uuagaaaggg guaucggcag aggcuugagu ugucugacau cuaccagauc    120
cccucgguag auucggcgga uaaccucucg gagaagcucg aacgggaaug ggaccgcgaa    180
cucgcgucua agaaaaaccc gaagcucauc aacgcacuga gaaggugcuu cuucggcgg    240 uucauguucu acgguaucuu cuuguaucuc ggggagguca caaaagcagu ccaaccccug    300 uuguggguc gcauuaucgc cucguacgac cccgauaaca agaagaacg gagcaucgcg     360 aucuaccucg ggaucggacu guguuugcuu uucaucguca gaacacuuuu guugcaucca    420
gcaaucuucg gccuccauca caucgguaug cagaugcgaa ucgcuauguu uagcuugauc    480
uacaaaaaga cacugaaacu cucgucgcgg guguuggaua agauuuccau cggucaguug    540
gugucccugc uuaguaauaa ccucaacaaa uucgaugagg gacuggcgcu ggcacauuuc    600
guguggauug ccccguugca agucgcccuu uugaugggcc uuauugggga gcuguugcag    660
gcaucugccu uugugggccu gggauuucug auugucuugg cauguuuuca ggcugggcuu    720 ggcggauga ugaugaagua ucgcgaccag agagcgggua aaaucucgga aagacucguc     780
aucacuucgg aaaugaucga aaacaucag ucggucaaag ccuauugcug ggaagaagcu    840
auggagaaga ugauugaaaa ccuccgccaa acugagcuga aacugacccg caaggcggcg    900
uaugaccggu auucaauuc gucagcguuc uucuuuccg gguucuucgu ugucuuucuc     960
ucgguuuugc cuuaugccuu gauuaagggg auuauccucc gcaagauuuu caccacgauu    1020
ucguucugca uuguauugcg cauggcagug acacggcaau uccgugggc cgucagaca    1080 uggauugacu cgcuuggagc gaucaacaaa auccaagacu ucuugcaaaa gcaagaguac    1140
aagacccugg aguacaaucu acuacuacg gagguaguaa uggagaaugu gacggcuuuu     1200
ugggaagagg guuuggaga acuguuugag aaagcaaagc agaauaacaa caaccgcaag    1260
accucaaaug gggacgauuc ccuguuuuuc ucgaacuucu cccugcucgg aacacccgug    1320
uugaaggaca ucaauuucaa gauugagagg ggacagcuuc ucgcgguagc gggaagcacu    1380
ggugcgggaa aaacuagccu cuugauggug auuauggggg agcuugagcc cagcgagggg    1440
aagauuaaac acuccgggcg uaucucauuc uguagccagu uucauggau caugcccgga    1500 accauuaaag agaacaucau uuucggagua uccauaaug aguaccgaua cagaucgguc     1560
auuaaggcgu gccaguugga agaggacauu ucuaaguucg ccgagaagga uaacaucguc    1620
uugggagaag ggguauuac auugucggga gggcagcgag cgcggaucag ccucgcgaga    1680
gcgguauaca aagaugcaga uuuguaucug cuugauucac cguuuggaua ccucgacgua    1740
uugacagaaa aagaaaucuu cgagucgugc guguguaaac uuauggcuaa uaagacgaga    1800 auccuggug caucaaaaau ggaacaccuu aagaaggcgg acaagauccu gauccuccac    1860
gaaggaucgu ccuacuuuua cggcacuuuc ucagaguugc aaaacuugca gccgacuuc    1920 ucaagcaaac ucauggggug ugacucauuc gaccaguuca gcgcggaacg gcggaacucg    1980
aucuugacgg aaacgcugca ccgauucucg cuugagggug augccccggu aucguggacc    2040
gagacaaaga agcagucguu uaagcagaca ggagaauuug gugagaaaag aaagaacagu    2100
aucuugaauc cuauuaacuc aauucgcaag uucucaaucg uccagaaaac uccacugcag    2160
augaauggaa uugaagagga uucgacgaa ccccuggagc gcaggcuuag ccucgugccg    2220
gauucagagc aaggggaggc cauucuuccc cggauuucgg ugauuucaac cggaccuaca    2280
cuucaggcga ggcgaaggca auccgugcuc aacccauga cgcaucggu aaaccagggg    2340 caaaacauuc accgcaaaac gacgccuca acgagaaaag ugucacugc accccaggcg    2400 aauuugacug aacucgacau cuacagccgu aggcuuucgc aagaaaccgg acuugagauc    2460
```

```
agcgaagaaa ucaaugaaga agauuugaaa gaguguuucu uugaugacau ggaaucaauc    2520
ccagcgguga caacguggaa cacauacuug cguuacauca cggugcacaa guccuugauu    2580
uucguccuca ucuggugucu cgugaucuuu cucgcugagg ucgcagcguc acuugguc      2640 cucuggcugc uugguaauac gcccuugcaa gacaaaggca auucuacaca cucaagaaac    2700
aauuccuaug ccgugauuau cacuucuaca agcucguauu acguguuuua caucacgua     2760 ggaguggccg acacucugcu cgcgaugggu ucuuccgag acucccacu cguucacacg       2820 cuuaucacug ucuccaagau ucuccaccau aagaugcuuc auagcguacu gcaggcuccc    2880
auguccaccu ugaauacgcu caaggcggga ggauauuuga aucgcuucuc aaaagauauu    2940
gcaauuuugg augaccuucu gccccugacg aucuucgacu ucauccaguu guugcugauc    3000
gugauugggg cuauugcagu agcgcguc cccagccuu acauuuugu cgcgaccguu          3060 ccggugaucg uggcguuuau caugcugcgg gccuauuucu ugcagacguc acagcagcuu    3120
aagcaacugg agucugaagg gaggucgccu aucuuuacgc aucuugugac caguuugaag    3180
ggauugugga cguugcgcgc cuuuggcagg cagcccuacu uugaaacacu guccacaaa     3240 gcgcugaauc uccauacggc aaauuggauu uuguauuuga guacccuccg augguuucag    3300
augcgcauug agaugauuuu ugugaucuuc uuuaucgcgg ugacuuuuau cuccaucuug    3360
accacgggag agggcgaggg acgggucggu auuauccuga cacucgccau gaacauuaug    3420
agcacuuugc aguggcagu gaacagcucg auugaugugg auagccugau gagguccguu      3480
ucgagggucu uuaaguucau cgacaugccg acggagggaa agcccacaaa aaguacgaaa    3540
cccuauaaga augggcaauu gaguaaggua augaucaucg agaacaguca cgugaagaag    3600
gaugacaucu ggccuagcgg gggucagaug accgugaagg accugacggc aaaauacacc    3660
gagggaggga acgcaauccu ugaaaacauc ucguucagca uuagcccgg ucagcgugug      3720 ggguugcucg ggaggaccgg gucaggaaaa ucgacguugc ugucggccuu cuugagacuu    3780
cugaauacag agggugagau ccagaucgac ggcguuucgu gggauagcau caccuugcag    3840
caguggcgga agcguuugg aguaaucccc caaaaggucu uuaucuuuag cggaaccuuc     3900
cgaaagaauc ucgauccuua ugaacagugg ucagaucaag agauuggaa agucgcggac     3960 gagguuggcc uucggagugu aaucgagcag uuuccgggaa aacucgacuu uguccuugua    4020 gauggggau gcguccuguc gcaugggcac aagcagcuca ugcgccuggc gcgauccguc      4080
cucucuaaag cgaaaauucu ucucuuggau gaaccuucgg cccaucugga cccgguaacg    4140
uaucagauca ucgaaaggac acuuaagcag gcguuugccg acugcacggu gauucucugu    4200
gagcaucgua ucgaggccau gcucgaaugc cagcaauuuc uugucaucga agagaauaag    4260
guccgccagu acgacuccau ccagaagcug cuuaaugaga gaucauuguu ccggcaggcg    4320
auuucaccau ccgauagggu gaaacuuuuu ccacacagaa auucgucgaa gugcaaguccc   4380 aaaccgcaga ucgcggccuu gaaagaagag acugaagaag aaguucaaga cacgcgucuu    4440
uaa                                                                  4443
```

<210> SEQ ID NO 9
<211> LENGTH: 140
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 9

```
ggacagaucg ccuggagacg ccauccacgc uguuuugacc uccauagaag acaccgggac      60
cgauccagcc uccgcggccg ggaacggugc auuggaacgc ggauucccccg ugccaagagu    120 gacucaccgu ccuugacacg                                                 140

<210> SEQ ID NO 10
<211> LENGTH: 105
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 10 cgggguggcau cccugugacc ccuccccagu gccucuccug gcccuggaag uugccacucc     60
agugcccacc agccuugucc uaauaaaauu aaguugcauc aagcu                     105
```

ENCAPSULATION OF MESSENGER RNA

CROSS-REFERENCE TO RELATED APPLICATIONS

This application claims priority to U.S. provisional patent application Ser. No. 62/020,163, filed Jul. 2, 2014, the disclosure of which is hereby incorporated in its entirety.

SEQUENCE LISTING

The instant application contains a Sequence Listing which has been submitted electronically in ASCII format and is hereby incorporated by reference in its entirety. Said ASCII copy, created on Aug. 12, 2015, is named 2006685-1078_SL.txt and is 20,862 bytes in size.

BACKGROUND

Messenger RNA therapy (MRT) is becoming an increasingly important approach for the treatment of a variety of diseases. MRT involves administration of messenger RNA (mRNA) into a patient in need of the therapy for production of the protein encoded by the mRNA within the patient body. Lipid nanoparticles are commonly used to encapsulate mRNA for efficient in vivo delivery of mRNA. However, current methods for producing mRNA-loaded lipid nanoparticles suffer poor encapsulation efficiency, low mRNA recovery and/or heterogeneous particle sizes.

SUMMARY OF INVENTION

The present invention provides, among other things, an improved process for lipid nanoparticle formulation and mRNA encapsulation. In particular, the present invention is based on the surprising discovery that pre-heating a mRNA solution and/or a lipid solution prior to mixing resulted in significantly improved encapsulation efficiency, mRNA recovery rate, and more homogeneous and smaller particle sizes (e.g., less than 100 nm).

Thus, in some embodiments, the present invention provides a process of encapsulating messenger RNA (mRNA) in lipid nanoparticles comprising a step of mixing a mRNA solution and a lipid solution, wherein the mRNA solution and/or the lipid solution are at a pre-determined temperature greater than ambient temperature. In some embodiments, a pre-determined temperature suitable for the present invention is or is greater than about 30° C., 37° C., 40° C., 45° C., 50° C., 55° C., 60° C., 65° C., or 70° C. In some embodiments, a pre-determined temperature suitable for the present invention ranges from about 25-70° C., about 30-70° C., about 35-70° C., about 40-70° C., about 45-70° C., about 50-70° C., or about 60-70° C. In particular embodiments, a pre-determined temperature suitable for the present invention is about 65° C.

In some embodiments, the mRNA solution and the lipid solution are heated to the pre-determined temperature separately prior to the mixing. In some embodiments, the mRNA solution is heated to the pre-determined temperature and the lipid solution is at ambient temperature prior to the mixing. In some embodiments, the mRNA solution is heated to the pre-determined temperature by adding a mRNA stock solution at ambient temperature to a heated buffering solution to the pre-determined temperature. In some embodiments, the buffering solution has a pH no greater than about 4.5 (e.g., no greater than about 4.4, 4.2, 4.0 or 3.8).

In some embodiments, the mRNA solution and the lipid solution are mixed by a pulse-less flow pump. In some embodiments, a suitable pump is a gear pump. In some embodiments, a suitable pump is a peristaltic pump. In some embodiments, a suitable pump is a centrifugal pump.

In some embodiments, the mRNA solution is mixed at a flow rate ranging from about 150-250 ml/minute, 250-500 ml/minute, 500-1000 ml/minute, 1000-2000 ml/minute, 2000-3000 ml/minute, 3000-4000 ml/minute, or 4000-5000 ml/minute. In some embodiments, the mRNA solution is mixed at a flow rate of about 200 ml/minute, about 500 ml/minute, about 1000 ml/minute, about 2000 ml/minute, about 3000 ml/minute, about 4000 ml/minute, or about 5000 ml/minute.

In some embodiments, the lipid solution is mixed at a flow rate ranging from about 25-75 ml/minute, about 75-200 ml/minute, about 200-350 ml/minute, about 350-500 ml/minute, about 500-650 ml/minute, about 650-850 ml/minute, or about 850-1000 ml/minute. In some embodiments, the lipid solution is mixed at a flow rate of about 50 ml/minute, about 100 ml/minute, about 150 ml/minute, about 200 ml/minute, about 250 ml/minute, about 300 ml/minute, about 350 ml/minute, about 400 ml/minute, about 450 ml/minute, about 500 ml/minute, about 550 ml/minute, about 600 ml/minute, about 650 ml/minute, about 700 ml/minute, about 750 ml/minute, about 800 ml/minute, about 850 ml/minute, about 900 ml/minute, about 950 ml/minute, or about 1000 ml/minute.

In some embodiments, a process according to the present invention includes a step of first generating the mRNA solution by mixing a citrate buffer with a mRNA stock solution. In certain embodiments, a suitable citrate buffer contains about 10 mM citrate, about 150 mM NaCl, pH of about 4.5. In some embodiments, a suitable mRNA stock solution contains the mRNA at a concentration at or greater than about 0.10 mg/mL, 1 mg/ml, about 10 mg/ml, about 50 mg/ml, or about 100 mg/ml.

In some embodiments, the citrate buffer is mixed at a flow rate ranging between about 100-300 ml/minute, 300-600 ml/minute, 600-1200 ml/minute, 1200-2400 ml/minute, 2400-3600 ml/minute, 3600-4800 ml/minute, or 4800-6000 ml/minute. In some embodiments, the citrate buffer is mixed at a flow rate of about 220 ml/minute, about 600 ml/minute, about 1200 ml/minute, about 2400 ml/minute, about 3600 ml/minute, about 4800 ml/minute, or about 6000 ml/minute.

In some embodiments, the mRNA stock solution is mixed at a flow rate ranging between about 10-30 ml/minute, about 30-60 ml/minute, about 60-120 ml/minute, about 120-240 ml/minute, about 240-360 ml/minute, about 360-480 ml/minute, or about 480-600 ml/minute. In some embodiments, the mRNA stock solution is mixed at a flow rate of about 20 ml/minute, about 40 ml/minute, about 60 ml/minute, about 80 ml/minute, about 100 ml/minute, about 200 ml/minute, about 300 ml/minute, about 400 ml/minute, about 500 ml/minute, or about 600 ml/minute.

In some embodiments, the lipid solution contains one or more cationic lipids, one or more helper lipids, one or more cholesterol-based lipids and PEG lipids in ethanol. In some embodiments, the mRNA solution and the lipid solution are mixed into a 20% ethanol, resulting in a suspension of lipid nanoparticles. In some embodiments, the lipid nanoparticles are further purified by Tangential Flow Filtration.

In some embodiments, greater than about 50%, 55%, 60%, 65%, 70%, 75%, 80%, 85%, 90%, 95%, 96%, 97%, 98%, or 99% of the purified nanoparticles have a size less than about 100 nm (e.g., less than about 95 nm, about 90 nm, about 85 nm, about 80 nm, about 75 nm, about 70 nm, about 65 nm, about 60 nm, about 55 nm, or about 50 nm). In some embodiments, substantially all of the purified nanoparticles have a size less than 100 nm (e.g., less than about 95 nm, about 90 nm, about 85 nm, about 80 nm, about 75 nm, about 70 nm, about 65 nm, about 60 nm, about 55 nm, or about 50 nm).

In some embodiments, greater than about 70%, 75%, 80%, 85%, 90%, 95%, 96%, 97%, 98%, 99% of the purified nanoparticles have a size ranging from about 40-90 nm (e.g., about 40-85 nm, about 40-80 nm, about 40-75 nm, about 40-70 nm, about 40-65 nm, or about 40-60 nm). In some embodiments, substantially all of the purified nanoparticles have a size ranging from about 40-90 nm (e.g., about 40-85 nm, about 40-80 nm, about 40-75 nm, about 40-70 nm, about 40-65 nm, or about 40-60 nm).

In some embodiments, the purified nanoparticles have an encapsulation efficiency of greater than about 80%, 85%, 90%, 95%, 96%, 97%, 98%, or 99%. In some embodiments, a process according to the present invention results in greater than about 60%, 65%, 70%, 75%, 80%, 85%, 90%, 95%, 96%, 97%, 98%, or 99% recovery of mRNA.

In some embodiments, the present invention provides a process of encapsulating messenger RNA (mRNA) in lipid nanoparticles, comprising (a) separately heating a mRNA solution and/or a lipid solution to a pre-determined temperature greater than ambient temperature; (b) mixing the heated mRNA solution and/or the heated lipid solution to generate a suspension of lipid nanoparticles; and (c) purifying the lipid nanoparticles.

In another aspect, the present invention provides a composition of lipid nanoparticles generated by a process described herein. In some embodiments, the present invention provides a composition comprising purified lipid nanoparticles, wherein greater than about 90% of the purified lipid nanoparticles have an individual particle size of less than about 100 nm (e.g., less than about 95 nm, about 90 nm, about 85 nm, about 80 nm, about 75 nm, about 70 nm, about 65 nm, about 60 nm, about 55 nm, or about 50 nm) and greater than about 70% of the purified lipid nanoparticles encapsulate a mRNA within each individual particle. In some embodiments, greater than about 95%, 96%, 97%, 98%, or 99% of the purified lipid nanoparticles have an individual particle size of less than about 100 nm (e.g., less than about 95 nm, about 90 nm, about 85 nm, about 80 nm, about 75 nm, about 70 nm, about 65 nm, about 60 nm, about 55 nm, or about 50 nm). In some embodiments, substantially all of the purified lipid nanoparticles have an individual particle size of less than about 100 nm (e.g., less than about 95 nm, about 90 nm, about 85 nm, about 80 nm, about 75 nm, about 70 nm, about 65 nm, about 60 nm, about 55 nm, or about 50 nm). In some embodiments, greater than about 75%, 80%, 85%, 90%, 95%, 96%, 97%, 98%, or 99% of the purified lipid nanoparticles encapsulate a mRNA within each individual particle. In some embodiments, substantially all of the purified lipid nanoparticles encapsulate a mRNA within each individual particle. In some embodiments, a composition according to the present invention contains at least about 1 mg, 5 mg, 10 mg, 100 mg, 500 mg, or 1000 mg of encapsulated mRNA.

In some embodiments, each individual lipid nanoparticle comprises one or more cationic lipids, one or more helper lipids, one or more cholesterol-based lipids and PEG lipids. In some embodiments, the one or more cationic lipids are selected from the group consisting of C12-200, MC3, DLinDMA, DLinkC2DMA, cKK-E12, ICE (Imidazol-based), HGT5000, HGT5001, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, HGT4003, and combinations thereof.

In some embodiments, the one or more non-cationic lipids are selected from DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (2-dioleoyl-sn-glycero-3-phospho-(1'-rac-glycerol)).

In some embodiments, the one or more cholesterol-based lipids is cholesterol or PEGylated cholesterol. In some embodiments, the one or more PEG-modified lipids contain a poly(ethylene)glycol chain of up to 5 kDa in length covalently attached to a lipid with alkyl chain(s) of $C_6$-$C_{20}$ length.

In some embodiments, the present invention is used to encapsulate mRNA containing one or more modified nucleotides. In some embodiments, the present invention is used to encapsulate mRNA that is unmodified.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWINGS

The drawings are for illustration purposes only and not for limitation.

FIG. 5: depicts an alternative schematic of an exemplary scaled-up lipid nanoparticle encapsulated mRNA formulation process with peristaltic pumps.

DEFINITIONS

Figure 1:
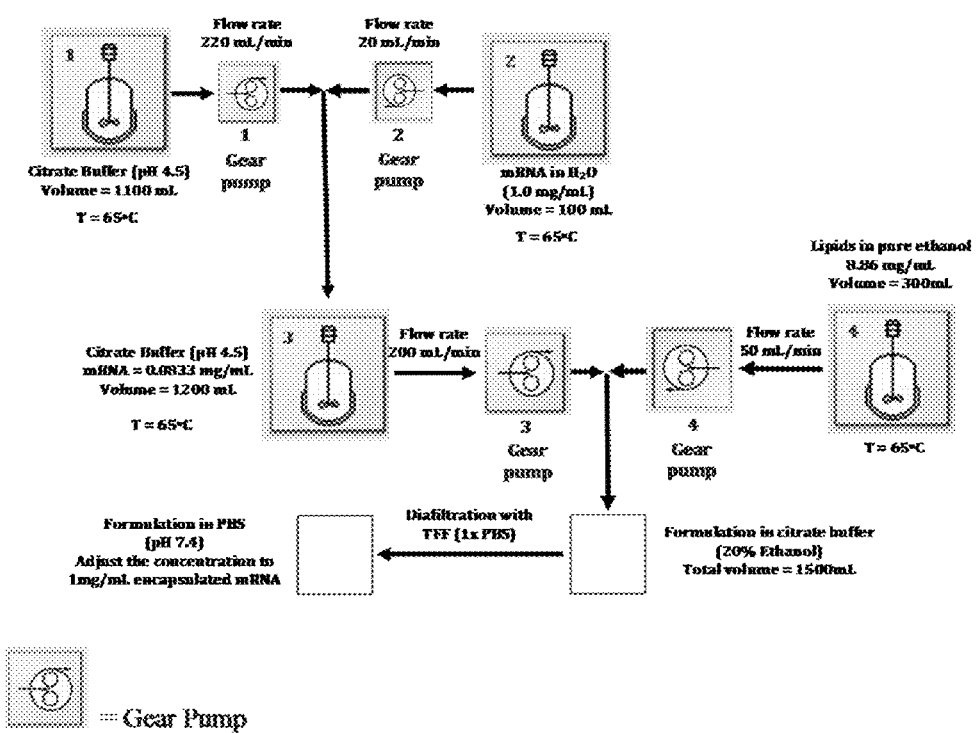
FIG. 1: shows a schematic of an exemplary scaled-up lipid nanoparticle encapsulated mRNA formulation process with homogenous flow pumps.

In order for the present invention to be more readily understood, certain terms are first defined below. Additional definitions for the following terms and other terms are set forth throughout the specification.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Encapsulation: As used herein, the term "encapsulation," or grammatical equivalent, refers to the process of confining an individual mRNA molecule within a nanoparticle.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

Impurities: As used herein, the term "impurities" refers to substances inside a confined amount of liquid, gas, or solid, which differ from the chemical composition of the target material or compound. Impurities are also referred to as contaminants.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions.

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Salt: As used herein the term "salt" refers to an ionic compound that does or may result from a neutralization reaction between an acid and a base.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Yield: As used herein, the term "yield" refers to the percentage of mRNA recovered after encapsulation as compared to the total mRNA as starting material. In some embodiments, the term "recovery" is used interchangeably with the term "yield".

DETAILED DESCRIPTION

The present invention provides an improved process for lipid nanoparticle formulation and mRNA encapsulation. In some embodiments, the present invention provides a process of encapsulating messenger RNA (mRNA) in lipid nanoparticles comprising a step of mixing a mRNA solution and a lipid solution, wherein the mRNA solution and/or the lipid solution are at a pre-determined temperature greater than ambient temperature.

Various aspects of the invention are described in detail in the following sections. The use of sections is not meant to limit the invention. Each section can apply to any aspect of the invention. In this application, the use of "or" means "and/or" unless stated otherwise.

mRNA

The present invention may be used to encapsulate any mRNA. mRNA is typically thought of as the type of RNA that carries information from DNA to the ribosome. The existence of mRNA is typically very brief and includes processing and translation, followed by degradation. Typically, in eukaryotic organisms, mRNA processing comprises the addition of a "cap" on the N-terminal (5') end, and a "tail" on the C-terminal (3') end. A typical cap is a 7-methylguanosine cap, which is a guanosine that is linked through a 5'-5'-triphosphate bond to the first transcribed nucleotide. The presence of the cap is important in providing resistance to nucleases found in most eukaryotic cells. The tail is typically a polyadenylation event whereby a polyadenylyl moiety is added to the 3' end of the mRNA molecule. The presence of this "tail" serves to protect the mRNA from exonuclease degradation. Messenger RNA is translated by the ribosomes into a series of amino acids that make up a protein.

mRNAs may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, in vitro synthesized mRNA may be purified before formulation and encapsulation to remove undesirable impurities including various enzymes and other reagents used during mRNA synthesis.

The present invention may be used to formulate and encapsulate mRNAs of a variety of lengths. In some embodiments, the present invention may be used to formulate and encapsulate in vitro synthesized mRNA of or greater than about 1 kb, 1.5 kb, 2 kb, 2.5 kb, 3 kb, 3.5 kb, 4 kb, 4.5 kb, 5 kb 6 kb, 7 kb, 8 kb, 9 kb, 10 kb, 11 kb, 12 kb, 13 kb, 14 kb, 15 kb, or 20 kb in length. In some embodiments, the present invention may be used to formulate and encapsulate in vitro synthesized mRNA ranging from about 1-20 kb, about 1-15 kb, about 1-10 kb, about 5-20 kb, about 5-15 kb, about 5-12 kb, about 5-10 kb, about 8-20 kb, or about 8-15 kb in length.

The present invention may be used to formulate and encapsulate mRNA that is unmodified or mRNA containing one or more modifications that typically enhance stability. In some embodiments, modifications are selected from modified nucleotide, modified sugar phosphate backbones, 5' and/or 3' untranslated region.

In some embodiments, modifications of mRNA may include modifications of the nucleotides of the RNA. An modified mRNA according to the invention can include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. No. 4,373,071, U.S. Pat. No. 4,401,796, U.S. Pat. No. 4,415,732, U.S. Pat. No. 4,458,066, U.S. Pat. No. 4,500,707, U.S. Pat. No. 4,668,777, U.S. Pat. No. 4,973,679, U.S. Pat. No. 5,047,524, U.S. Pat. No. 5,132,418, U.S. Pat. No. 5,153,319, U.S. Pat. Nos. 5,262,530 and 5,700,642, the disclosure of which is included here in its full scope by reference.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. 2'-O-methylation may also occur at the first base and/or second base following the 7-methyl guanosine triphosphate residues. Examples of cap structures include, but are not limited to, m7GpppNp-RNA, m7GpppNmp-RNA and m7GpppNmpNmp-RNA (where m indicates 2'-Omethyl residues).

In some embodiments, mRNAs include a 5' and/or 3' untranslated region. In some embodiments, a 5' untranslated region includes one or more elements that affect a mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect a mRNA's stability of location in a cell, or one or more binding sites for miRNAs. In some embodiments, a 3' untranslated region may be between 50 and 500 nucleotides in length or longer.

While mRNA provided from in vitro transcription reactions may be desirable in some embodiments, other sources of mRNA are contemplated as within the scope of the invention including mRNA produced from bacteria, fungi, plants, and/or animals.

The present invention may be used to formulate and encapsulate mRNAs encoding a variety of proteins. Non-limiting examples of mRNAs suitable for the present invention include mRNAs encoding spinal motor neuron 1

(SMN), alpha-galactosidase (GLA), argininosuccinate synthetase (ASS1), firefly luciferase, Factor IX (FIX), phenylalanine hydroxylase (PAH), and cystic fibrosis transmembrane conductance receptor (CFTR). Exemplary mRNA sequences are described in detail in the Examples section.

mRNA Solution mRNA may be provided in a solution to be mixed with a lipid solution such that the mRNA may be encapsulated in lipid nanoparticles. A suitable mRNA solution may be any aqueous solution containing mRNA to be encapsulated at various concentrations. For example, a suitable mRNA solution may contain a mRNA at a concentration of or greater than about 0.01 mg/ml, 0.05 mg/ml, 0.06 mg/ml, 0.07 mg/ml, 0.08 mg/ml, 0.09 mg/ml, 0.1 mg/ml, 0.15 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1.0 mg/ml. In some embodiments, a suitable mRNA solution may contain a mRNA at a concentration ranging from about 0.01-1.0 mg/ml, 0.01-0.9 mg/ml, 0.01-0.8 mg/ml, 0.01-0.7 mg/ml, 0.01-0.6 mg/ml, 0.01-0.5 mg/ml, 0.01-0.4 mg/ml, 0.01-0.3 mg/ml, 0.01-0.2 mg/ml, 0.01-0.1 mg/ml, 0.05-1.0 mg/ml, 0.05-0.9 mg/ml, 0.05-0.8 mg/ml, 0.05-0.7 mg/ml, 0.05-0.6 mg/ml, 0.05-0.5 mg/ml, 0.05-0.4 mg/ml, 0.05-0.3 mg/ml, 0.05-0.2 mg/ml, 0.05-0.1 mg/ml, 0.1-1.0 mg/ml, 0.2-0.9 mg/ml, 0.3-0.8 mg/ml, 0.4-0.7 mg/ml, or 0.5-0.6 mg/ml. In some embodiments, a suitable mRNA solution may contain a mRNA at a concentration up to about 5.0 mg/ml, 4.0 mg/ml, 3.0 mg/ml, 2.0 mg/ml, 1.0 mg/ml, 0.09 mg/ml, 0.08 mg/ml, 0.07 mg/ml, 0.06 mg/ml, or 0.05 mg/ml.

Typically, a suitable mRNA solution may also contain a buffering agent and/or salt. Generally, buffering agents can include HEPES, ammonium sulfate, sodium bicarbonate, sodium citrate, sodium acetate, potassium phosphate and sodium phosphate. In some embodiments, suitable concentration of the buffering agent may range from about 0.1 mM to 100 mM, 0.5 mM to 90 mM, 1.0 mM to 80 mM, 2 mM to 70 mM, 3 mM to 60 mM, 4 mM to 50 mM, 5 mM to 40 mM, 6 mM to 30 mM, 7 mM to 20 mM, 8 mM to 15 mM, or 9 to 12 mM. In some embodiments, suitable concentration of the buffering agent is or greater than about 0.1 mM, 0.5 mM, 1 mM, 2 mM, 4 mM, 6 mM, 8 mM, 10 mM, 15 mM, 20 mM, 25 mM, 30 mM, 35 mM, 40 mM, 45 mM, or 50 mM.

Exemplary salts can include sodium chloride, magnesium chloride, and potassium chloride. In some embodiments, suitable concentration of salts in a mRNA solution may range from about 1 mM to 500 mM, 5 mM to 400 mM, 10 mM to 350 mM, 15 mM to 300 mM, 20 mM to 250 mM, 30 mM to 200 mM, 40 mM to 190 mM, 50 mM to 180 mM, 50 mM to 170 mM, 50 mM to 160 mM, 50 mM to 150 mM, or 50 mM to 100 mM. Salt concentration in a suitable mRNA solution is or greater than about 1 mM, 5 mM, 10 mM, 20 mM, 30 mM, 40 mM, 50 mM, 60 mM, 70 mM, 80 mM, 90 mM, or 100 mM.

In some embodiments, a suitable mRNA solution may have a pH ranging from about 3.5-6.5, 3.5-6.0, 3.5-5.5, 3.5-5.0, 3.5-4.5, 4.0-5.5, 4.0-5.0, 4.0-4.9, 4.0-4.8, 4.0-4.7, 4.0-4.6, or 4.0-4.5. In some embodiments, a suitable mRNA solution may have a pH of or no greater than about 3.5, 4.0, 4.1, 4.2, 4.3, 4.4, 4.5, 4.6, 4.7, 4.8, 4.9, 5.0, 5.2, 5.4, 5.6, 5.8, 6.0, 6.1, 6.3, and 6.5.

Various methods may be used to prepare a mRNA solution suitable for the present invention. In some embodiments, mRNA may be directly dissolved in a buffering solution described herein. In some embodiments, a mRNA solution may be generated by mixing a mRNA stock solution with a buffering solution prior to mixing with a lipid solution for encapsulation. In some embodiments, a mRNA solution may be generated by mixing a mRNA stock solution with a buffering solution immediately before mixing with a lipid solution for encapsulation. In some embodiments, a suitable mRNA stock solution may contain mRNA in water at a concentration at or greater than about 0.2 mg/ml, 0.4 mg/ml, 0.5 mg/ml, 0.6 mg/ml, 0.8 mg/ml, 1.0 mg/ml, 1.2 mg/ml, 1.4 mg/ml, 1.5 mg/ml, or 1.6 mg/ml, 2.0 mg/ml, 2.5 mg/ml, 3.0 mg/ml, 3.5 mg/ml, 4.0 mg/ml, 4.5 mg/ml, or 5.0 mg/ml.

In some embodiments, a mRNA stock solution is mixed with a buffering solution using a pump. Exemplary pumps include but are not limited to gear pumps, peristaltic pumps and centrifugal pumps.

Typically, the buffering solution is mixed at a rate greater than that of the mRNA stock solution. For example, the buffering solution may be mixed at a rate at least 1×, 2×, 3×, 4×, 5×, 6×, 7×, 8×, 9×, 10×, 15×, or 20× greater than the rate of the mRNA stock solution. In some embodiments, a buffering solution is mixed at a flow rate ranging between about 100-6000 ml/minute (e.g., about 100-300 ml/minute, 300-600 ml/minute, 600-1200 ml/minute, 1200-2400 ml/minute, 2400-3600 ml/minute, 3600-4800 ml/minute, 4800-6000 ml/minute, or 60-420 ml/minute). In some embodiments, a buffering solution is mixed at a flow rate of or greater than about 60 ml/minute, 100 ml/minute, 140 ml/minute, 180 ml/minute, 220 ml/minute, 260 ml/minute, 300 ml/minute, 340 ml/minute, 380 ml/minute, 420 ml/minute, 480 ml/minute, 540 ml/minute, 600 ml/minute, 1200 ml/minute, 2400 ml/minute, 3600 ml/minute, 4800 ml/minute, or 6000 ml/minute.

In some embodiments, a mRNA stock solution is mixed at a flow rate ranging between about 10-600 ml/minute (e.g., about 5-50 ml/minute, about 10-30 ml/minute, about 30-60 ml/minute, about 60-120 ml/minute, about 120-240 ml/minute, about 240-360 ml/minute, about 360-480 ml/minute, or about 480-600 ml/minute). In some embodiments, a mRNA stock solution is mixed at a flow rate of or greater than about 5 ml/minute, 10 ml/minute, 15 ml/minute, 20 ml/minute, 25 ml/minute, 30 ml/minute, 35 ml/minute, 40 ml/minute, 45 ml/minute, 50 ml/minute, 60 ml/minute, 80 ml/minute, 100 ml/minute, 200 ml/minute, 300 ml/minute, 400 ml/minute, 500 ml/minute, or 600 ml/minute.

Lipid Solution

According to the present invention, a lipid solution contains a mixture of lipids suitable to form lipid nanoparticles for encapsulation of mRNA. In some embodiments, a suitable lipid solution is ethanol based. For example, a suitable lipid solution may contain a mixture of desired lipids dissolved in pure ethanol (i.e., 100% ethanol). In another embodiment, a suitable lipid solution is isopropyl alcohol based. In another embodiment, a suitable lipid solution is dimethylsulfoxide-based. In another embodiment, a suitable lipid solution is a mixture of suitable solvents including, but not limited to, ethanol, isopropyl alcohol and dimethylsulfoxide.

A suitable lipid solution may contain a mixture of desired lipids at various concentrations. For example, a suitable lipid solution may contain a mixture of desired lipids at a total concentration of or greater than about 0.1 mg/ml, 0.5 mg/ml, 1.0 mg/ml, 2.0 mg/ml, 3.0 mg/ml, 4.0 mg/ml, 5.0 mg/ml, 6.0 mg/ml, 7.0 mg/ml, 8.0 mg/ml, 9.0 mg/ml, 10 mg/ml, 15 mg/ml, 20 mg/ml, 30 mg/ml, 40 mg/ml, 50 mg/ml, or 100 mg/ml. In some embodiments, a suitable lipid solution may contain a mixture of desired lipids at a total concentration ranging from about 0.1-100 mg/ml, 0.5-90 mg/ml, 1.0-80 mg/ml, 1.0-70 mg/ml, 1.0-60 mg/ml, 1.0-50 mg/ml, 1.0-40 mg/ml, 1.0-30 mg/ml, 1.0-20 mg/ml, 1.0-15 mg/ml, 1.0-10 mg/ml, 1.0-9 mg/ml, 1.0-8 mg/ml, 1.0-7 mg/ml, 1.0-6 mg/ml, or 1.0-5 mg/ml. In some embodiments, a suitable lipid solution may contain a mixture of desired lipids at a total concentration up to about 100 mg/ml, 90 mg/ml, 80 mg/ml, 70 mg/ml, 60 mg/ml, 50 mg/ml, 40 mg/ml, 30 mg/ml, 20 mg/ml, or 10 mg/ml.

Any desired lipids may be mixed at any ratios suitable for encapsulating mRNAs. In some embodiments, a suitable lipid solution contain a mixture of desired lipids including cationic lipids, helper lipids (e.g. non cationic lipids and/or cholesterol lipids) and/or PEGylated lipids. In some embodiments, a suitable lipid solution contain a mixture of desired lipids including one or more cationic lipids, one or more helper lipids (e.g. non cationic lipids and/or cholesterol lipids) and one or more PEGylated lipids.

Cationic Lipids

As used herein, the phrase "cationic lipids" refers to any of a number of lipid species that have a net positive charge at a selected pH, such as physiological pH. Several cationic lipids have been described in the literature, many of which are commercially available. Particularly suitable cationic lipids for use in the compositions and methods of the invention include those described in international patent publications WO 2010/053572 (and particularly, C12-200 described at paragraph [00225]) and WO 2012/170930, both of which are incorporated herein by reference. In certain embodiments, cationic lipids suitable for the compositions and methods of the invention include an ionizable cationic lipid described in U.S. provisional patent application 61/617,468, filed Mar. 29, 2012 (incorporated herein by reference), such as, e.g., (15Z,18Z)—N,N-dimethyl-6-(9Z,12Z)-octadeca-9,12-dien-1-yl)tetracosa-15,18-dien-1-amine (HGT5000), (15Z,18Z)—N,N-dimethyl-6-((9Z,12Z)-octadeca-9,12-dien-1-yl)tetracosa-4,15,18-trien-1-amine (HGT5001), and (15Z,18Z)—N,N-dimethyl-6-((9Z,12Z)-octadeca-9,12-dien-1-yl)tetracosa-5,15,18-trien-1-amine (HGT5002).

In some embodiments, cationic lipids suitable for the compositions and methods of the invention include a cationic lipid described in WO 2013063468 and in U.S. provisional application entitled "Lipid Formulations for Delivery of Messenger RNA" both of which are incorporated by reference herein. In some embodiments, a cationic lipid comprises a compound of formula I-c1-a:

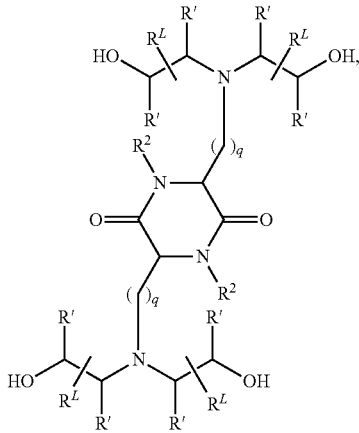

I-c1-a or a pharmaceutically acceptable salt thereof, wherein:
each $R^2$ independently is hydrogen or $C_{1-3}$ alkyl;
each q independently is 2 to 6;
each R' independently is hydrogen or $C_{1-3}$ alkyl;
and each $R^L$ independently is $C_{8-12}$ alkyl.

In some embodiments, each $R^2$ independently is hydrogen, methyl or ethyl. In some embodiments, each $R^2$ independently is hydrogen or methyl. In some embodiments, each $R^2$ is hydrogen.

In some embodiments, each q independently is 3 to 6. In some embodiments, each q independently is 3 to 5. In some embodiments, each q is 4.

In some embodiments, each R' independently is hydrogen, methyl or ethyl. In some embodiments, each R' independently is hydrogen or methyl. In some embodiments, each R' independently is hydrogen.

In some embodiments, each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ independently is n-$C_{10}$ alkyl.

In some embodiments, each $R^2$ independently is hydrogen or methyl; each q independently is 3 to 5; each R' independently is hydrogen or methyl; and each $R^L$ independently is $C_{8-12}$ alkyl.

In some embodiments, each $R^2$ is hydrogen; each q independently is 3 to 5; each R' is hydrogen; and each $R^L$ independently is $C_{8-12}$ alkyl.

In some embodiments, each $R^2$ is hydrogen; each q is 4; each R' is hydrogen; and each $R^L$ independently is $C_{8-12}$ alkyl.

In some embodiments, a cationic lipid comprises a compound of formula I-g:

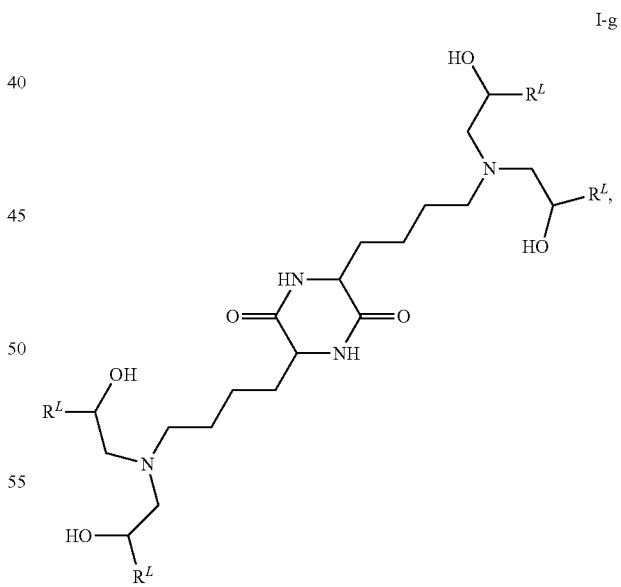

I-g or a pharmaceutically acceptable salt thereof, wherein each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ is n-$C_{10}$ alkyl.

In particular embodiments, a suitable cationic lipid is cKK-E12, or (3,6-bis(4-(bis(2-hydroxydodecyl)amino)butyl)piperazine-2,5-dione). Structure of cKK-E12 is shown below:

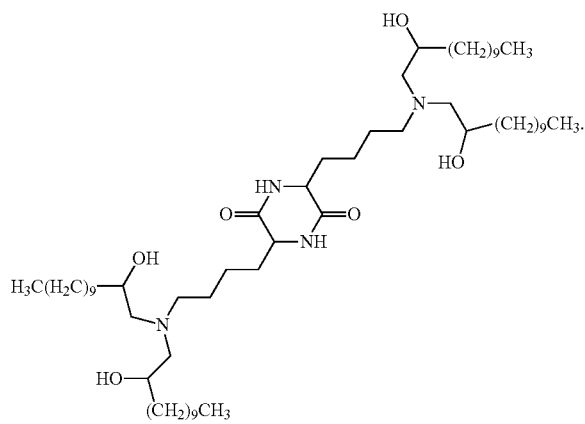

In some embodiments, one or more cationic lipids suitable for the present invention may be N-[1-(2,3-dioleyloxy)propyl]-N,N,N-trimethylammonium chloride or "DOTMA". (Feigner et al. (Proc. Nat'l Acad. Sci. 84, 7413 (1987); U.S. Pat. No. 4,897,355). Other suitable cationic lipids include, for example, 5-carboxyspermylglycinedioctadecylamide or "DOGS," 2,3-dioleyloxy-N-[2(sperminecarboxamido)ethyl]-N,N-dimethyl-1-propanaminium or "DOSPA" (Behr et al. Proc. Nat'l Acad. Sci. 86, 6982 (1989); U.S. Pat. No. 5,171,678; U.S. Pat. No. 5,334,761), 1,2-Dioleoyl-3-Dimethylammonium-Propane or "DODAP", 1,2-Dioleoyl-3-Trimethylammonium-Propane or "DOTAP".

Additional exemplary cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylammonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethyl-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin-DMA", 2,2-dilinoleyl-4-dimethylaminoethyl-[1,3]-dioxolane or "DLin-K-XTC2-DMA", and 2-(2,2-di((9Z,12Z)-octadeca-9,12-dien-1-yl)-1,3-dioxolan-4-yl)-N,N-dimethylethanamine (DLin-KC2-DMA)) (see, WO 2010/042877; Semple et al., Nature Biotech. 28: 172-176 (2010)), or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1). In some embodiments, one or more of the cationic lipids comprise at least one of an imidazole, dialkylamino, or guanidinium moiety.

In some embodiments, one or more cationic lipids may be chosen from XTC (2,2-Dilinoleyl-4-dimethylaminoethyl-[1,3]-dioxolane), MC3 (((6Z,9Z,28Z,31Z)-heptatriaconta-6,9,28,31-tetraen-19-yl 4-(dimethylamino)butanoate), ALNY-100 ((3aR,5s,6aS)—N,N-dimethyl-2,2-di((9Z,12Z)-octadeca-9,12-dienyl)tetrahydro-3aH-cyclopenta[d][1,3]dioxol-5-amine)), NC98-5 (4,7,13-tris(3-oxo-3-(undecylamino)propyl)-N1,N16-diundecyl-4,7,10,13-tetraazahexadecane-1,16-diamide), DODAP (1,2-dioleyl-3-dimethylammonium propane), HGT4003 (WO 2012/170889, the teachings of which are incorporated herein by reference in their entirety), ICE (WO 2011/068810, the teachings of which are incorporated herein by reference in their entirety), HGT5000 (U.S. Provisional Patent Application No. 61/617,468, the teachings of which are incorporated herein by reference in their entirety) or HGT5001 (cis or trans) (Provisional Patent Application No. 61/617,468), aminoalcohol lipidoids such as those disclosed in WO2010/053572, DOTAP (1,2-dioleyl-3-trimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869).

In some embodiments, cationic lipids constitute at least about 5%, 10%, 20%, 30%, 35%, 40%, 45%, 50%, 55%, 60%, 65%, or 70% of the total lipids in a suitable lipid solution by weight or by molar. In some embodiments, cationic lipid(s) constitute(s) about 30-70% (e.g., about 30-65%, about 30-60%, about 30-55%, about 30-50%, about 30-45%, about 30-40%, about 35-50%, about 35-45%, or about 35-40%) of the total lipid mixture by weight or by molar.

Non-Cationic/Helper Lipids

As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

In some embodiments, non-cationic lipids may constitute at least about 5%, 10%, 15%, 20%, 25%, 30%, 35%, 40%, 45%, 50%, 55%, 60%, 65% or 70% of the total lipids in a suitable lipid solution by weight or by molar. In some embodiments, non-cationic lipid(s) constitute(s) about 30-50% (e.g., about 30-45%, about 30-40%, about 35-50%, about 35-45%, or about 35-40%) of the total lipids in a suitable lipid solution by weight or by molar.

Cholesterol-Based Lipids

In some embodiments, a suitable lipid solution include one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, cholesterol-based lipid(s) constitute(s) at least about 5%, 10%, 20%, 30%, 40%, 50%, 60%, or 70% of the total lipids in a suitable lipid solution by weight or by molar. In some embodiments, cholesterol-based lipid(s) constitute(s) about 30-50% (e.g., about 30-45%, about 30-40%, about 35-50%, about 35-45%, or about 35-40%) of the total lipids in a suitable lipid solution by weight or by molar.

PEGylated Lipids

In some embodiments, a suitable lipid solution includes one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl (Methoxy Polyethylene Glycol)-2000] (C8 PEG-2000 ceramide) is also contemplated by the present invention. Contemplated PEG-modified lipids include, but are not limited to, a polyethylene glycol chain of up to 5 kDa in length covalently attached to a lipid with alkyl chain(s) of $C_6$-$C_{20}$ length. In some embodiments, a PEG-modified or PEGylated lipid is PEGylated cholesterol or PEG-2K. In some embodiments, particularly useful exchangeable lipids are PEG-ceramides having shorter acyl chains (e.g., $C_{14}$ or $C_{18}$).

PEG-modified phospholipid and derivatized lipids may constitute at least about 5%, 10%, 20%, 30%, 40%, 50%, 60%, or 70% of the total lipids in a suitable lipid solution by weight or by molar. In some embodiments, PEGylated lipid lipid(s) constitute(s) about 30-50% (e.g., about 30-45%, about 30-40%, about 35-50%, about 35-45%, or about 35-40%) of the total lipids in a suitable lipid solution by weight or by molar.

Exemplary combinations of cationic lipids, non-cationic lipids, cholesterol-based lipids, and PEG-modified lipids are described in the Examples section. For example, a suitable lipid solution may contain cKK-E12, DOPE, chol, and DMG-PEG2K; C12-200, DOPE, cholesterol, and DMG-PEG2K; HGT5000, DOPE, chol, and DMG-PEG2K; HGT5001, DOPE, chol, and DMG-PEG2K; cKK-E12, DPPC, chol, and DMG-PEG2K; C12-200, DPPC, cholesterol, and DMG-PEG2K; HGT5000, DPPC, chol, and DMG-PEG2K; or HGT5001, DPPC, chol, and DMG-PEG2K. The selection of cationic lipids, non-cationic lipids and/or PEG-modified lipids which comprise the lipid mixture as well as the relative molar ratio of such lipids to each other, is based upon the characteristics of the selected lipid(s) and the nature of the and the characteristics of the mRNA to be encapsulated. Additional considerations include, for example, the saturation of the alkyl chain, as well as the size, charge, pH, pKa, fusogenicity and toxicity of the selected lipid(s). Thus the molar ratios may be adjusted accordingly.

Mixing Process

The present invention is based on the discovery of unexpected effect of temperature on the mRNA encapsulation efficiency and recovery rate. Thus, in some embodiments, the present invention provides a process of encapsulating messenger RNA (mRNA) in lipid nanoparticles by mixing a mRNA solution and a lipid solution, described herein, wherein the mRNA solution and/or the lipid solution are heated to a pre-determined temperature greater than ambient temperature. As used herein, the term "ambient temperature" refers to the temperature in a room, or the temperature which surrounds an object of interest (e.g., a mRNA solution or lipid solution) without heating or cooling. In some embodiments, the ambient temperature refers to temperature ranging from about 20-25° C.

Therefore, a pre-determined temperature greater than ambient temperature is typically greater than about 25° C. In some embodiments, a pre-determined temperature suitable for the present invention is or is greater than about 30° C., 37° C., 40° C., 45° C., 50° C., 55° C., 60° C., 65° C., or 70° C. In some embodiments, a pre-determined temperature suitable for the present invention ranges from about 25-70° C., about 30-70° C., about 35-70° C., about 40-70° C., about 45-70° C., about 50-70° C., or about 60-70° C. In particular embodiments, a pre-determined temperature suitable for the present invention is about 65° C.

The mRNA solution, or the lipid solution, or both, may be heated to a pre-determined temperature above the ambient temperature prior to mixing. In some embodiments, the mRNA solution and the lipid solution are heated to the pre-determined temperature separately prior to the mixing. In some embodiments, the mRNA solution and the lipid solution are mixed at the ambient temperature but then heated to the pre-determined temperature after the mixing. In some embodiments, the lipid solution is heated to the pre-determined temperature and mixed with a mRNA solution at the ambient temperature. In some embodiments, the mRNA solution is heated to the pre-determined temperature and mixed with a lipid solution at ambient temperature.

In some embodiments, the mRNA solution is heated to the pre-determined temperature by adding a mRNA stock solution that is at ambient temperature to a heated buffering solution to achieve the desired pre-determined temperature.

A mRNA solution and a lipid solution may be mixed using a pump. As the encapsulation procedure can occur on a wide range of scales, different types of pumps may be used to accommodate desired scale. It is however generally desired to use a pulse-less flow pumps. As used herein, a pulse-less flow pump refers to any pump that can establish a continuous flow with a stable flow rate. Types of suitable pumps may include, but are not limited to, gear pumps and centrifugal pumps. Exemplary gear pumps include, but are not limited to, Cole-Parmer or Diener gear pumps. Exemplary centrifugal pumps include, but are not limited to, those manufactured by Grainger or Cole-Parmer.

A mRNA solution and a lipid solution may be mixed at various flow rates. Typically, the mRNA solution may be mixed at a rate greater than that of the lipid solution. For example, the mRNA solution may be mixed at a rate at least 1×, 2×, 3×, 4×, 5×, 6×, 7×, 8×, 9×, 10×, 15×, or 20× greater than the rate of the lipid solution.

Suitable flow rates for mixing may be determined based on the scales. In some embodiments, a mRNA solution is mixed at a flow rate ranging from about 40-400 ml/minute, 60-500 ml/minute, 70-600 ml/minute, 80-700 ml/minute, 90-800 ml/minute, 100-900 ml/minute, 110-1000 ml/minute, 120-1100 ml/minute, 130-1200 ml/minute, 140-1300 ml/minute, 150-1400 ml/minute, 160-1500 ml/minute, 170-1600 ml/minute, 180-1700 ml/minute, 150-250 ml/minute, 250-500 ml/minute, 500-1000 ml/minute, 1000-2000 ml/minute, 2000-3000 ml/minute, 3000-4000 ml/minute, or 4000-5000 ml/minute. In some embodiments, the mRNA solution is mixed at a flow rate of about 200 ml/minute, about 500 ml/minute, about 1000 ml/minute, about 2000 ml/minute, about 3000 ml/minute, about 4000 ml/minute, or about 5000 ml/minute.

In some embodiments, a lipid solution is mixed at a flow rate ranging from about 25-75 ml/minute, 20-50 ml/minute, 25-75 ml/minute, 30-90 ml/minute, 40-100 ml/minute, 50-110 ml/minute, 75-200 ml/minute, 200-350 ml/minute, 350-500 ml/minute, 500-650 ml/minute, 650-850 ml/minute, or 850-1000 ml/minute. In some embodiments, the lipid solution is mixed at a flow rate of about 50 ml/minute, about 100 ml/minute, about 150 ml/minute, about 200 ml/minute, about 250 ml/minute, about 300 ml/minute, about 350 ml/minute, about 400 ml/minute, about 450 ml/minute, about 500 ml/minute, about 550 ml/minute, about 600 ml/minute, about 650 ml/minute, about 700 ml/minute, about 750 ml/minute, about 800 ml/minute, about 850 ml/minute, about 900 ml/minute, about 950 ml/minute, or about 1000 ml/minute.

Typically, a mRNA solution and a lipid solution are mixed into a solution such that the lipids can form nanoparticles encapsulating mRNA. Such a solution is also referred to as a formulation or encapsulation solution. A suitable formulation or encapsulation solution may be based on a solvent such as ethanol. For example, a suitable formulation or encapsulation solution may be based on about 10% ethanol, about 15% ethanol, about 20% ethanol, about 25% ethanol, about 30% ethanol, about 35% ethanol, or about 40% ethanol.

A suitable formulation or encapsulation solution may be based on a solvent such as isopropyl alcohol. For example, a suitable formulation or encapsulation solution may be based on about 10% isopropyl alcohol, about 15% isopropyl alcohol, about 20% isopropyl alcohol, about 25% isopropyl alcohol, about 30% isopropyl alcohol, about 35% isopropyl alcohol, or about 40% isopropyl alcohol.

A suitable formulation or encapsulation solution may be based on a solvent such as dimethyl sulfoxide. For example, a suitable formulation or encapsulation solution may be based on about 10% dimethyl sulfoxide, about 15% dimethyl sulfoxide, about 20% dimethyl sulfoxide, about 25% dimethyl sulfoxide, about 30% dimethyl sulfoxide, about 35% dimethyl sulfoxide, or about 40% dimethyl sulfoxide.

A suitable formulation or encapsulation solution may also contain a buffering agent or salt. Exemplary buffering agent may include HEPES, ammonium sulfate, sodium bicarbonate, sodium citrate, sodium acetate, potassium phosphate and sodium phosphate. Exemplary salt may include sodium chloride, magnesium chloride, and potassium chloride.

Purification

Typically, subsequent to formulation and encapsulation, lipid nanoparticles are purified and/or concentrated. Various purification methods may be used. In some embodiments, lipid nanoparticles are purified using Tangential Flow Filtration. Tangential flow filtration (TFF), also referred to as cross-flow filtration, is a type of filtration wherein the material to be filtered is passed tangentially across a filter rather than through it. In TFF, undesired permeate passes through the filter, while the desired retentate passes along the filter and is collected downstream. It is important to note that the desired material is typically contained in the retentate in TFF, which is the opposite of what one normally encounters in traditional-dead end filtration.

Depending upon the material to be filtered, TFF is usually used for either microfiltration or ultrafiltration. Microfiltration is typically defined as instances where the filter has a pore size of between 0.05 μm and 1.0 μm, inclusive, while ultrafiltration typically involves filters with a pore size of less than 0.05 μm. Pore size also determines the nominal molecular weight limits (NMWL), also referred to as the molecular weight cut off (MWCO) for a particular filter, with microfiltration membranes typically having NMWLs of greater than 1,000 kilodaltons (kDa) and ultrafiltration filters having NMWLs of between 1 kDa and 1,000 kDa.

A principal advantage of tangential flow filtration is that non-permeable particles that may aggregate in and block the filter (sometimes referred to as "filter cake") during traditional "dead-end" filtration, are instead carried along the surface of the filter. This advantage allows tangential flow filtration to be widely used in industrial processes requiring continuous operation since down time is significantly reduced because filters do not generally need to be removed and cleaned.

Tangential flow filtration can be used for several purposes including concentration and diafiltration, among others. Concentration is a process whereby solvent is removed from a solution while solute molecules are retained. In order to effectively concentrate a sample, a membrane having a NMWL or MWCO that is substantially lower than the molecular weight of the solute molecules to be retained is used. Generally, one of skill may select a filter having a NMWL or MWCO of three to six times below the molecular weight of the target molecule(s).

Diafiltration is a fractionation process whereby small undesired particles are passed through a filter while larger desired nanoparticles are maintained in the retentate without changing the concentration of those nanoparticles in solution. Diafiltration is often used to remove salts or reaction buffers from a solution. Diafiltration may be either continuous or discontinuous. In continuous diafiltration, a diafiltration solution is added to the sample feed at the same rate that filtrate is generated. In discontinuous diafiltration, the solution is first diluted and then concentrated back to the starting concentration. Discontinuous diafiltration may be repeated until a desired concentration of nanoparticles is reached.

Purified and/or concentrated lipid nanoparticles may be formulated in a desired buffer such as, for example, PBS.

Provided Nanoparticles Encapsulating mRNA

A process according to the present invention results in more homogeneous and smaller particle sizes (e.g., less than 100 nm), as well as significantly improved encapsulation efficiency and/or mRNA recovery rate as compared to a prior art process.

Thus, the present invention provides a composition comprising purified nanoparticles described herein. In some embodiments, majority of purified nanoparticles in a composition, i.e., greater than about 50%, 55%, 60%, 65%, 70%, 75%, 80%, 85%, 90%, 95%, 96%, 97%, 98%, or 99% of the purified nanoparticles, have a size less than about 100 nm (e.g., less than about 95 nm, about 90 nm, about 85 nm, about 80 nm, about 75 nm, about 70 nm, about 65 nm, about 60 nm, about 55 nm, or about 50 nm). In some embodiments, substantially all of the purified nanoparticles have a size less than 100 nm (e.g., less than about 95 nm, about 90 nm, about 85 nm, about 80 nm, about 75 nm, about 70 nm, about 65 nm, about 60 nm, about 55 nm, or about 50 nm).

In addition, more homogeneous nanoparticles with narrow particle size range are achieved by a process of the present invention. For example, greater than about 70%, 75%, 80%, 85%, 90%, 95%, 96%, 97%, 98%, 99% of the purified nanoparticles in a composition provided by the present invention have a size ranging from about 40-90 nm (e.g., about 40-85 nm, about 40-80 nm, about 40-75 nm, about 40-70 nm, about 40-65 nm, or about 40-60 nm). In some embodiments, substantially all of the purified nanoparticles have a size ranging from about 40-90 nm (e.g., about 40-85 nm, about 40-80 nm, about 40-75 nm, about 40-70 nm, about 40-65 nm, or about 40-60 nm).

In some embodiments, the dispersity, or measure of heterogeneity in size of molecules (PDI), of nanoparticles in a composition provided by the present invention is less than about 0.16 (e.g., less than about 0.15, 0.14, 0.13, 0.12, 0.11, 0.10, 0.09, or 0.08).

In some embodiments, greater than about 75%, 80%, 85%, 90%, 95%, 96%, 97%, 98%, or 99% of the purified lipid nanoparticles in a composition provided by the present invention encapsulate a mRNA within each individual particle. In some embodiments, substantially all of the purified lipid nanoparticles in a composition encapsulate a mRNA within each individual particle.

In some embodiments, a composition according to the present invention contains at least about 1 mg, 5 mg, 10 mg, 100 mg, 500 mg, or 1000 mg of encapsulated mRNA. In some embodiments, a process according to the present invention results in greater than about 60%, 65%, 70%, 75%, 80%, 85%, 90%, 95%, 96%, 97%, 98%, or 99% recovery of mRNA.

EXAMPLES

While certain compounds, compositions and methods of the present invention have been described with specificity in accordance with certain embodiments, the following examples serve only to illustrate the compounds of the invention and are not intended to limit the same.

Example 1

Effect of Temperature on Nanoparticle Encapsulation Process

This example demonstrates that an increase in temperature during nanoparticle encapsulation process results in increased yield and/or encapsulation efficiency.

Lipid Materials

The formulations described in the following Examples, unless otherwise specified, contain a multi-component lipid mixture of varying ratios employing one or more cationic lipids, helper lipids (e.g., non-cationic lipids and/or cholesterol lipids) and PEGylated lipids designed to encapsulate various nucleic acid materials. Cationic lipids for the process can include but are not limited to DOTAP (1,2-dioleyl-3-trimethylammonium propane), DODAP (1,2-dioleyl-3-dimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869), cKK-E12 (3,6-bis(4-(bis(2-hydroxydodecyl)amino)butyl)piperazine-2,5-dione), HGT5000, HGT5001, HGT4003, ICE, dialkylamino-based, imidazole-based, guanidinium-based, etc. Helper lipids can include but are not limited to DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (2-dioleoyl-sn-glycero-3-phospho-(1'-rac-glycerol)), cholesterol, etc. The PEGylated lipids can include but are not limited to a poly(ethylene) glycol chain of up to 5 kDa in length covalently attached to a lipid with alkyl chain(s) of C6-C20 length.

Messenger RNA Material

Codon-optimized human spinal motor neuron 1 (SMN) messenger RNA, argininosuccinate synthetase (ASS1) messenger RNA, modified cystic fibrosis transmembrane conductance regulator (SNIM® CFTR, 25% pseudouridine, 25% 5-methyl-cytidine) messenger RNA, firefly luciferase (FFL) messenger RNA, Factor IX (FIX) messenger RNA, phelyalanine hydroxylase (PAH) messenger RNA and alpha-galactosidase (GLA) messenger RNA was synthesized by in vitro transcription from a plasmid DNA template encoding the gene, which was followed by the addition of a 5' cap structure (Cap 1) (Fechter, P.; Brownlee, G. G. "Recognition of mRNA cap structures by viral and cellular proteins" J. Gen. Virology 2005, 86, 1239-1249) and a 3' poly(A) tail of approximately 250 nucleotides in length (SEQ ID NO: 1) as determined by gel electrophoresis. 5' and 3' untranslated regions present in each mRNA product are represented as X and Y, respectively and defined as stated (vide infra).

Codon-Optimized Human Spinal Motor Neuron 1 (SMN) mRNA:
(SEQ ID NO: 2)
XAUGGCCAUGAGCAGCGGAGGCAGCGGCGGAGGAGUGCCCGAGCAGGAGG

ACAGCGUGCUGUUCAGGAGAGGCACCGGCCAGAGCGAUGACAGCGAUAUC

UGGGACGAUACCGCUCUGAUCAAGGCCUACGACAAGGCCGUGGCCAGCUU

CAAGCACGCCCUGAAAAACGGCGACAUCUGCGAGACCAGCGGCAAGCCCA

AGACAACCCCCAAGAGAAAGCCCGCCAAGAAGAAUAAGAGCCAGAAAAAG

AACACCGCCGCCAGCCUGCAGCAGUGGAAGGUGGGCGACAAGUGCAGCGC

CAUCUGGAGCGAGGACGGCUGCAUCUACCCCGCCACCAUCGCCAGCAUCG

ACUUCAAGAGAGAGACCUGCGUGGUCGUGUACACCGGCUACGGCAACAGA

GAGGAGCAGAACCUGAGCGACCUGCUGAGCCCCAUUUGUGAGGUGGCCAA

UAACAUCGAACAGAACGCCCAGGAGAACGAGAAUGAAAGCCAGGUGAGCA

CCGACGAGAGCGAGAACAGCAGAUCUCCUGGCAACAAGAGCGACAACAUC

AAGCCUAAGUCUGCCCCUUGGAACAGCUUCCUGCCCCCUCCUCCACCCAU

GCCCGGACCCAGACUGGGACCCGGAAAACCUGGCCUGAAGUUCAACGGAC

CACCUCCCCUCCACCUCCUCCCCCACCUCAUCUCCUGAGCUGCUGGCUG

CCACCCUUCCCCAGCGGACCCCCUAUCAUCCCACCACCCCCUCCCAUCUG

CCCCGACAGCCUGGACGACGCCGAUGCCCUGGGCAGCAUGCUGAUCAGCU

GGUACAUGAGCGGCUACCACACAGGAUACUACAUGGGCUUCAGACAGAAC

CAGAAGGAGGGCAGAUGCUCCCACUCCCUGAACUGAY

Human alpha-galactosidase (GLA) mRNA:
(SEQ ID NO: 3)
XAUGCAGCUGAGGAACCCAGAACUACAUCUGGGCUGCGCGCUUGCGCUUC

GCUUCCUGGCCCUCGUUUCCUGGGACAUCCCUGGGGCUAGAGCACUGGAC

AAUGGAUUGGCAAGGACGCCUACCAUGGGCUGGCUGCACUGGGAGCGCUU

CAUGUGCAACCUUGACUGCCAGGAAGAGCCAGAUUCCUGCAUCAGUGAGA

AGCUCUUCAUGGAGAUGGCAGAGCUCAUGGUCUCAGAAGGCUGGAAGGAU

GCAGGUUAUGAGUACCUCUGCAUUGAUGACUGUUGGAUGGCUCCCCAAAG

```
AGAUUCAGAAGGCAGACUUCAGGCAGACCCUCAGCGCUUUCCUCAUGGGA

UUCGCCAGCUAGCUAAUUAUGUUCACAGCAAAGGACUGAAGCUAGGGAUU

UAUGCAGAUGUUGGAAAUAAAACCUGCGCAGGCUUCCCUGGGAGUUUUGG

AUACUACGACAUUGAUGCCCAGACCUUUGCUGACUGGGGAGUAGAUCUGC

UAAAAUUUGAUGGUUGUUACUGUGACAGUUUGGAAAAUUUGGCAGAUGGU

UAUAAGCACAUGUCCUUGGCCCUGAAUAGGACUGGCAGAAGCAUUGUGUA

CUCCUGUGAGUGGCCUCUUUAUAUGUGGCCCUUUCAAAAGCCCAAUUAUA

CAGAAAUCCGACAGUACUGCAAUCACUGGCGAAAUUUUGCUGACAUUGAU

GAUUCCUGGAAAAGUAUAAAGAGUAUCUUGGACUGGACAUCUUUUAACCA

GGAGAGAAUUGUUGAUGUUGCUGGACCAGGGGGUUGGAAUGACCCAGAUA

UGUUAGUGAUUGGCAACUUUGGCCUCAGCUGGAAUCAGCAAGUAACUCAG

AUGGCCCUCUGGGCUAUCAUGGCUGCUCCUUUAUUCAUGUCUAAUGACCU

CCGACACAUCAGCCCUCAAGCCAAAGCUCUCCUUCAGGAUAAGGACGUAA

UUGCCAUCAAUCAGGACCCCUUGGGCAAGCAAGGGUACCAGCUUAGACAG

GGAGACAACUUUGAAGUGUGGGAACGACCUCUCUCAGGCUUAGCCUGGGC

UGUAGCUAUGAUAAACCGGCAGGAGAUUGGUGGACCUCGCUCUUAUACCA

UCGCAGUUGCUUCCCUGGGUAAAGGAGUGGCCUGUAAUCCUGCCUGCUUC

AUCACACAGCUCCUCCCUGUGAAAAGGAAGCUAGGGUUCUAUGAAUGGAC

UUCAAGGUUAAGAAGUCACAUAAAUCCCACAGGCACUGUUUUGCUUCAGC

UAGAAAAUACAAUGCAGAUGUCAUUAAAAGACUUACUUUAAY

Codon-Optimized Human Argininosuccinate
Synthetase (ASS1) mRNA:
                                   (SEQ ID NO: 4)
XAUGAGCAGCAAGGGCAGCGUGGUGCUGGCCUACAGCGGCGGCCUGGACA

CCAGCUGCAUCCUGGUGUGGCUGAAGGAGCAGGGCUACGACGUGAUCGCC

UACCUGGCCAACAUCGGCCAGAAGGAGGACUUCGAGGAGGCCCGCAAGAA

GGCCCUGAAGCUGGGCGCCAAGAAGGUGUUCAUCGAGGACGUGAGCCGCG

AGUUCGUGGAGGAGUUCAUCUGGCCCGCCAUCCAGAGCAGCGCCCUGUAC

GAGGACCGCUACCUGCUGGGCACCAGCCUGGCCCGCCCCUGCAUCGCCCG

CAAGCAGGUGGAGAUCGCCCAGCGCGAGGGCGCCAAGUACGUGAGCCACG

GCGCCACCGGCAAGGGCAACGACCAGGUGCGCUUCGAGCUGAGCUGCUAC

AGCCUGGCCCCCCAGAUCAAGGUGAUCGCCCCCUGGCGCAUGCCCGAGUU

CUACAACCGCUUCAAGGGCCGCAACGACCUGAUGGAGUACGCCAAGCAGC

ACGGCAUCCCCAUCCCCGUGACCCCCAAGAACCCCUGGAGCAUGGACGAG

AACCUGAUGCACAUCAGCUACGAGGCCGGCAUCCUGGAGAACCCCAAGAA

CCAGGCCCCCCCGGCCUGUACACCAAGACCCAGGACCCCGCCAAGGCCC

CCAACACCCCCGACAUCCUGGAGAUCGAGUUCAAGAAGGGCGUGCCCGUG

AAGGUGACCAACGUGAAGGACGGCACCACCCACCAGACCAGCCUGGAGCU

GUUCAUGUACCUGAACGAGGUGGCCGGCAAGCACGGCGUGGGCCGCAUCG

ACAUCGUGGAGAACCGCUUCAUCGGCAUGAAGAGCCGCGGCAUCUACGAG

ACCCCCGCCGGCACCAUCCUGUACCACGCCCACCUGGACAUCGAGGCCUU

CACCAUGGACCGCGAGGUGCGCAAGAUCAAGCAGGGCCUGGGCCUGAAGU

UCGCCGAGCUGGUGUACACCGGCUUCUGGCACAGCCCCGAGUGCGAGUUC

GUGCGCCACUGCAUCGCCAAGAGCCAGGAGCGCGUGGAGGGCAAGGUGCA

GGUGAGCGUGCUGAAGGGCCAGGUGUACAUCCUGGGCCGCGAGAGCCCCC

UGAGCCUGUACAACGAGGAGCUGGUGAGCAUGAACGUGCAGGGCGACUAC

GAGCCCACCGACGCCACCGGCUUCAUCAACAUCAACAGCCUGCGCCUGAA

GGAGUACCACCGCCUGCAGAGCAAGGUGACCGCCAAGUGAY

Codon-Optimized Firefly Luciferase mRNA:
                                   (SEQ ID NO: 5)
XAUGGAAGAUGCCAAAAACAUUAAGAAGGGCCCAGCGCCAUUCUACCCAC

UCGAAGACGGGACCGCCGGCGAGCAGCUGCACAAAGCCAUGAAGCGCUAC

GCCCUGGUGCCCGGCACCAUCGCCUUUACCGACGCACAUAUCGAGGUGGA

CAUUACCUACGCCGAGUACUUCGAGAUGAGCGUUCGGCUGGCAGAAGCUA

UGAAGCGCUAUGGGCUGAAUACAAACCAUCGGAUCGUGGUGUGCAGCGAG

AAUAGCUUGCAGUUCUUCAUGCCCGUGUUGGGUGCCCUGUUCAUCGGUGU

GGCUGUGGCCCCAGCUAACGACAUCUACAACGAGCGCGAGCUGCUGAACA

GCAUGGGCAUCAGCCAGCCACCGUCGUAUUCGUGAGCAAGAAAGGGCUG

CAAAAGAUCCUCAACGUGCAAAAGAAGCUACCGAUCAUACAAAAGAUCAU

CAUCAUGGAUAGCAAGACCGACUACCAGGGCUUCCAAAGCAUGUACACCU

UCGUGACUUCCCAUUUGCCACCCGGCUUCAACGAGUACGACUUCGUGCCC

GAGAGCUUCGACCGGGACAAAACCAUCGCCCUGAUCAUGAACAGUAGUGG

CAGUACCGGAUUGCCCAAGGGCGUAGCCCUACCGCACCGCACCGCUUGUG

UCCGAUUCAGUCAUGCCCGCGACCCCAUCUUCGGCAACCAGAUCAUCCCC

GACACCGCUAUCCUCAGCGUGGUGCCAUUUCACCACGGCUUCGGCAUGUU

CACCACGCUGGGCUACUUGAUCUGCGGCUUUCGGGUCGUGCUCAUGUACC

GCUUCGAGGAGGAGCUAUUCUUGCGCAGCUUGCAAGACUAUAAGAUUCAA

UCUGCCCUGCUGGUGCCCACACUAUUUAGCUUCUUCGCUAAGAGCACUCU

CAUCGACAAGUACGACCUAAGCAACUUGCACGAGAUCGCCAGCGGCGGGG

CGCCGCUCAGCAAGGAGGUAGGUGAGGCCGUGGCCAAACGCUUCCACCUA

CCAGGCAUCCGCCAGGGCUACGGCCUGACAGAAACAACCAGCGCCAUUCU

GAUCACCCCCGAAGGGGACGACAAGCCUGGCGCAGUAGGCAAGGUGGCUGU

CCUUCUUCGAGGCUAAGGUGGUGGACUUGGACACCGGUAAGACACUGGGU

GUGAACCAGCGCGGCGAGCUGUGCGUCCGUGGCCCCAUGAUCAUGAGCGG

CUACGUUAACAACCCCGAGGCUACAAACGCUCUCAUCGACAAGGACGGCU

GGCUGCACAGCGGCGACAUCGCCUACUGGGACGAGGACGAGCACUUCUUC

AUCGUGGACCGGCUGAAGAGCCUGAUCAAAUACAAGGGCUACCAGGUAGC

CCCAGCCGAACUGGAGAGCAUCCUGCUGCAACACCCCAACAUCUUCGACG

CCGGGGUCGCCGGCCUGCCCGACGACGAUGCCGGCGAGCUGCCCGCCGCA

GUCGUCGUGCUGGAACACGGUAAAACCAUGACCGAGAAGGAGAUCGUGGA

CUAUGUGGCCAGCCAGGUUACAACCGCCAAGAAGCUGCGCGGUGGUGUUG

UGUUCGUGGACGAGGUGCCUAAAGGACUGACCGGCAAGUUGGACGCCCGC

AAGAUCCGCGAGAUUCUCAUUAAGGCCAAGAAGGGCGGCAAGAUCGCCGU

GUAAY
```

Human Factor IX (FIX) mRNA:
(SEQ ID NO: 6)
XAUGCAGCGCGUGAACAUGAUCAUGGCAGAAUCACCAGGCCUCAUCACCA

UCUGCCUUUUAGGAUAUCUACUCAGUGCUGAAUGUACAGUUUUUCUUGAU

CAUGAAAACGCCAACAAAAUUCUGAGGCGGAGAAGGAGGUAUAAUUCAGG

UAAAUUGGAAGAGUUUGUUCAAGGGAACCUUGAGAGAGAAUGUAUGGAAG

AAAAGUGUAGUUUUGAAGAAGCACGAGAAGUUUUUGAAAACACUGAAAGA

ACAACUGAAUUUUGGAAGCAGUAUGUUGAUGGAGAUCAGUGUGAGUCCAA

UCCAUGUUUAAAUGGCGGCAGUUGCAAGGAUGACAUUAAUUCCUAUGAAU

GUUGGUGUCCCUUUGGAUUUGAAGGAAAGAACUGUGAAUUAGAUGUAACA

UGUAACAUUAAGAAUGGCAGAUGCGAGCAGUUUUGUAAAAAUAGUGCUGA

UAACAAGGUGGUUUGCUCCUGUACUGAGGGAUAUCGACUUGCAGAAAACC

AGAAGUCCUGUGAACCAGCAGUGCCAUUUCCAUGUGGAAGAGUUUCUGUU

UCACAAACUUCUAAGCUCACCCGUGCUGAGGCUGUUUUUCCUGAUGUGGA

CUAUGUAAAUUCUACUGAAGCUGAAACCAUUUUGGAUAACAUCACUCAAA

GCACCCAAUCAUUUAAUGACUUCACUCGGGUUGUUGGUGGAGAAGAUGCC

AAACCAGGUCAAUUCCCUUGGCAGGUUGUUUUGAAUGGUAAAGUUGAUGC

AUUCUGUGGAGGCUCUAUCGUUAAUGAAAAAUGGAUUGUAACUGCUGCCC

ACUGUGUUGAAACUGGUGUUAAAAUUACAGUUGUCGCAGGUGAACAUAAU

AUUGAGGAGACAGAACAUACAGAGCAAAAGCGAAAUGUGAUUCGAAUUAU

UCCUCACCACAACUACAAUGCAGCUAUUAAUAAGUACAACCAUGACAUUG

CCCUUCUGGAACUGGACGAACCCUUAGUGCUAAACAGCUACGUUACACCU

AUUUGCAUUGCUGACAAGGAAUACACGAACAUCUUCCUCAAAUUUGGAUC

UGGCUAUGUAAGUGGCUGGGGAAGAGUCUUCCACAAAGGGAGAUCAGCUU

UAGUUCUUCAGUACCUUAGAGUUCCACUUGUUGACCGAGCCACAUGUCUU

CGAUCUACAAAGUUCACCAUCUAUAACAACAUGUUCUGUGCUGGCUUCCA

UGAAGGAGGUAGAGAUUCAUGUCAAGGAGAUAGUGGGGGACCCCAUGUUA

CUGAAGUGGAAGGGACCAGUUUCUUAACUGGAAUUAUUAGCUGGGGUGAA

GAGUGUGCAAUGAAAGGCAAAUAUGGAAUAUAUACCAAGGUAUCCCGGUA

UGUCAACUGGAUUAAGGAAAAAACAAAGCUCACUUAAY

Codon-Optimized Human Phenylalanine Hydroxylase
(PAH) mRNA:
(SEQ ID NO: 7)
XAUGAGCACCGCCGUGCUGGAGAACCCCGGCCUGGGCCGCAAGCUGAGCG

ACUUCGGCCAGGAGACCAGCUACAUCGAGGACAACUGCAACCAGAACGGC

GCCAUCAGCCUGAUCUUCAGCCUGAAGGAGGAGGUGGGCGCCCUGGCCAA

GGUGCUGCGCCUGUUCGAGGAGAACGACGUGAACCUGACCCACAUCGAGA

GCCGCCCCAGCCGCCUGAAGAAGGACGAGUACGAGUUCUUCACCCACCUG

GACAAGCGCAGCCUGCCCGCCCUGACCAACAUCAUCAAGAUCCUGCGCCA

CGACAUCGGCGCCACCGUGCACGAGCUGAGCCGCGACAAGAAGAAGGACA

CCGUGCCCUGGUUCCCCCGCACCAUCCAGGAGCUGGACCGCUUCGCCAAC

CAGAUCCUGAGCUACGGCGCCGAGCUGGACGCCGACCACCCCGGCUUCAA

GGACCCCGUGUACCGCGCCCGCCGCAAGCAGUUCGCCGACAUCGCCUACA

ACUACCGCCACGGCCAGCCCAUCCCCCGCGUGGAGUACAUGGAGGAGGAG

AAGAAGACCUGGGGCACCGUGUUCAAGACCCUGAAGAGCCUGUACAAGAC

CCACGCCUGCUACGAGUACAACCACAUCUUCCCCCUGCUGGAGAAGUACU

GCGGCUUCCACGAGGACAACAUCCCCCAGCUGGAGGACGUGAGCCAGUUC

CUGCAGACCUGCACCGGCUUCCGCCUGCGCCCCGUGGCCGGCCUGCUGAG

CAGCCGCGACUUCCUGGGCGGCCUGGCCUUCCGCGUGUUCCACUGCACCC

AGUACAUCCGCCACGGCAGCAAGCCCAUGUACACCCCCGAGCCCGACAUC

UGCCACGAGCUGCUGGGCCACGUGCCCCUGUUCAGCGACCGCAGCUUCGC

CCAGUUCAGCCAGGAGAUCGGCCUGGCCAGCCUGGGCGCCCCCGACGAGU

ACAUCGAGAAGCUGGCCACCAUCUACUGGUUCACCGUGGAGUUCGGCCUG

UGCAAGCAGGGCGACAGCAUCAAGGCCUACGGCGCCGGCCUGCUGAGCAG

CUUCGGCGAGCUGCAGUACUGCCUGAGCGAGAAGCCCAAGCUGCUGCCCC

UGGAGCUGGAGAAGACCGCCAUCCAGAACUACACCGUGACCGAGUUCCAG

CCCCUGUACUACGUGGCCGAGAGCUUCAACGACGCCAAGGAGAAGGUGCG

CAACUUCGCCGCCACCAUCCCCCGCCCCUUCAGCGUGCGCUACGACCCCU

ACACCCAGCGCAUCGAGGUGCUGGACAACACCCAGCAGCUGAAGAUCCUG

GCCGACAGCAUCAACAGCGAGAUCGGCAUCCUGUGCAGCGCCCUGCAGAA

GAUCAAGUAAY

Codon-Optimized Cystic Fibrosis Transmembrane
Conductance Regulator (CFTR) mRNA:
(SEQ ID NO: 8)
AUGCAGCGGUCCCCGCUCGAAAAGGCCAGUGUCGUGUCCAAACUCUUCUU

CUCAUGGACUCGGCCUAUCCUUAGAAAGGGGUAUCGGCAGAGGCUUGAGU

UGUCUGACAUCUACCAGAUCCCCUCGGUAGAUUCGGCGGAUAACCUCUCG

GAGAAGCUCGAACGGGAAUGGGACCGCGAACUCGCGUCUAAGAAAAACCC

GAAGCUCAUCAACGCACUGAGAAGGUGCUUCUUCUGGCGGUUCAUGUUCU

ACGGUAUCUUCUUGUAUCUCGGGGAGGUCACAAAAGCAGUCCAACCCCUG

UUGUUGGGUCGCAUUAUCGCCUCGUACGACCCCGAUAACAAAGAAGAACG

GAGCAUCGCGAUCUACCUCGGGAUCGGACUGUGUUUGCUUUUCAUCGUCA

GAACACUUUUGUUGCAUCCAGCAAUCUUCGGCCUCCAUCACAUCGGUAUG

CAGAUGCGAAUCGCUAUGUUUAGCUUGAUCUACAAAAAGACACUGAAACU

CUCGUCGCGGGUGUUGGAUAAGAUUUCCAUCGGUCAGUUGGUGUCCCUGC

UUAGUAAUAACCUCAACAAAUUCGAUGAGGGACUGGCGCUGGCACAUUUC

GUGUGGAUUGCCCCGUUGCAAGUCGCCCUUUUGAUGGGCCUUAUUUGGGA

GCUGUUGCAGGCAUCUGCCUUUUGUGGCCUGGGAUUUCUGAUUGUGUUGG

CAUUGUUUCAGGCUGGGCUUGGCGGAUGAUGAUGAGUAUCGCGACCAG

AGAGCGGGUAAAAUCUCGGAAAGACUCGUCAUCACUUCGGAAAUGAUCGA

AAACAUCCAGUCGGUCAAAGCCUAUUGCUGGGAAGAAGCUAUGGAGAAGA

UGAUUGAAAACCUCCGCCAAACUGAGCUGAAACUGACCCGCAAGGCGGCG

UAUGUCCGGUAUUUCAAUCGUCAGCGUUCUUCUUUUCCGGGUUCUUCGU

UGUCUUUCUCUCGGUUUUGCCUUAUGCCUUGAUUAAGGGGAUUAUCCUCC

-continued

GCAAGAUUUUCACCACGAUUUCGUUCUGCAUUGUAUUGCGCAUGGCAGUG

ACACGGCAAUUUCCGUGGGCCGUGCAGACAUGGUAUGACUCGCUUGGAGC

GAUCAACAAAAUCCAAGACUUCUUGCAAAAGCAAGAGUACAAGACCCUGG

AGUACAAUCUUACUACUACGGAGGUAGUAAUGGAGAAUGUGACGGCUUUU

UGGGAAGAGGGUUUUGGAGAACUGUUUGAGAAAGCAAAGCAGAAUAACAA

CAACCGCAAGACCUCAAAUGGGGACGAUUCCCUGUUUUUCUCGAACUUCU

CCCUGCUCGGAACACCCGUGUUGAAGGACAUCAAUUUCAAGAUUGAGAGG

GGACAGCUUCUCGCGGUAGCGGGAAGCACUGGUGCGGGAAAAACUAGCCU

CUUGAUGGUGAUUAUGGGGGAGCUUGAGCCCAGCGAGGGGAAGAUUAAAC

ACUCCGGGCGUAUCUCAUUCUGUAGCCAGUUUUCAUGGAUCAUGCCCGGA

ACCAUUAAAGAGAACAUCAUUUUCGGAGUAUCCUAUGAUGAGUACCGAUA

CAGAUCGGUCAUUAAGGCGUGCCAGUUGGAAGAGGACAUUUCUAAGUUCG

CCGAGAAGGAUAACAUCGUCUUGGGAGAAGGGGUAUUACAUUGUCGGGA

GGGCAGCGAGCGCGGAUCAGCCUCGCGAGAGCGGUAUACAAAGAUGCAGA

UUUGUAUCUGCUUGAUUCACCGUUUGGAUACCUCGACGUAUUGACAGAAA

AAGAAAUCUUCGAGUCGUGCGUGUGUAAACUUAUGGCUAAUAAGACGAGA

AUCCUGGUGACAUCAAAAAUGGAACACCUUAAGAAGGCGGACAAGAUCCU

GAUCCUCCACGAAGGAUCGUCCUACUUUUACGGCACUUUCUCAGAGUUGC

AAAACUUGCAGCCGGACUUCUCAAGCAAACUCAUGGGGUGUGACUCAUUC

GACCAGUUCAGCGCGGAACGGCGGAACUCGAUCUUGACGGAAACGCUGCA

CCGAUUCUCGCUUGAGGGUGAUGCCCCGGUAUCGUGGACCGAGACAAAGA

AGCAGUCGUUUAAGCAGACAGGAGAAUUUGGUGAGAAAGAAAGAACAGU

AUCUUGAAUCCUAUUAACUCAAUUCGCAAGUUCUCAAUCGUCCAGAAAAC

UCCACUGCAGAUGAAUGGAAUUGAAGAGGAUUCGGACGAACCCCUGGAGC

GCAGGCUUAGCCUCGUGCCGGAUUCAGAGCAAGGGGAGGCCAUUCUUCCC

CGGAUUUCGGUGAUUUCAACCGGACCUACACUUCAGGCGAGGCGAAGGCA

AUCCGUGCUCAACCUCAUGACGCAUUCGGUAAACCAGGGGCAAAACAUUC

ACCGCAAAACGACGGCCUCAACGAGAAAAGUGUCACUUGCACCCCAGGCG

AAUUUGACUGAACUCGACAUCUACAGCCGUAGGCUUUCGCAAGAAACCGG

ACUUGAGAUCAGCGAAGAAAUCAAUGAAGAAGAUUUGAAAGAGUGUUUCU

UUGAUGACAUGGAAUCAAUCCCAGCGGUGACAACGUGGAACACAUACUUG

CGUUACAUCACGGUGCACAAGUCCUUGAUUUUCGUCCUCAUCGGUGUCU

CGUGAUCUUUCUCGCUGAGGUCGCAGCGUCACUUGUGGUCCUCUGGCUGC

UUGGUAAUACGCCCUUGCAAGACAAAGGCAAUUCUACACACUCAAGAAAC

AAUUCCUAUGCCGUGAUUAUCACUUCUACAAGCUCGUAUUACGUGUUUUA

CAUCUACGUAGGAGUGGCCGACACUCUGCUCGCGAUGGGUUUCUUCCGAG

GACUCCCACUCGUUCACACGCUUAUCACUGUCUCCAAGAUUCUCCACCAU

AAGAUGCUUCAUAGCGUACUGCAGGCUCCCAUGUCCACCUUGAAUACGCU

CAAGGCGGGAGGUAUUUUGAAUCGCUUCUCAAAAGAUAUUGCAAUUUUGG

AUGACCUUCUGCCCCUGACGAUCUUCGACUUCAUCCAGUUGUUGCUGAUC

-continued

GUGAUUGGGCUAUUGCAGUAGUCGCUGUCCUCCAGCCUUACAUUUUUGU

CGCGACCGUUCCGGUGAUCGUGGCGUUUAUCAUGCUGCGGGCCUAUUUCU

UGCAGACGUCACAGCAGCUUAAGCAACUGGAGUCUGAAGGGAGGUCGCCU

AUCUUUACGCAUCUUGUGACCAGUUUGAAGGGAUUGUGGACGUUGCGCGC

CUUUGGCAGGCAGCCCUACUUUGAAACACUGUUCCACAAAGCGCUGAAUC

UCCAUACGGCAAAUUGGUUUUUGUAUUUGAGUACCCUCCGAUGGUUUUCA

GAUGCGCAUUGAGAUGAUUUUUGUGAUCUUCUUUAUCGCGGUGACUUUUA

UCUCCAUCUUGACCACGGGAGAGGGCGAGGGACGGGUCGGUAUUAUCCUG

ACACUCGCCAUGAACAUUAUGAGCACUUUGCAGUGGGCAGUGAACAGCUC

GAUUGAUGUGGAUAGCCUGAUGAGGUCCGUUUCGAGGGGUCUUUAAGUUCA

UCGACAUGCCGACGGAGGGAAAGCCCACAAAAAGUACGAAACCCUAUAAG

AAUGGGCAAUUGAGUAAGGUAAUGAUCAUCGAGAACAGUCACGUGAAGAA

GGAUGACAUCUGGCCUAGCGGGGGUCAGAUGACCGUGAAGGACCUGACGG

CAAAAUACACCGAGGGAGGGAACGCAAUCCUUGAAAACAUCUCGUUCAGC

AUUAGCCCCGGUCAGCGUGUGGGGUUGCUCGGGAGGACCGGGUCAGGAAA

AUCGACGUUGCUGUCGGCCUUCUUGAGACUUCUGAAUACAGAGGGUGAGA

UCCAGAUCGACGGCGUUUCGUGGGAUAGCAUCACCUUGCAGCAGUGGCGG

AAAGCGUUUGGAGUAAUCCCCCAAAAGGUCUUUAUCUUUAGCGGAACCUU

CCGAAAGAAUCUCGAUCCUUAUGAACAGUGGUCAGAUCAAGAGAUUUGGA

AAGUCGCGGACGAGGUUGGCCUUCGGAGUGUAAUCGAGCAGUUUCCGGGA

AAACUCGACUUUGUCCUUGUAGAUGGGGGAUGCGUCCUGUCGCAUGGGCA

CAAGCAGCUCAUGUGCCUGGCGCGAUCCGUCCUCUCUAAAGCGAAAAUUC

UUCUCUUGGAUGAACCUUCGGCCCAUCUGGACCCGGUAACGUAUCAGAUC

AUCAGAAGGACACUUAAGCAGGCGUUUGCCGACUGCACGGUGAUUCUCUG

UGAGCAUCGUAUCGAGGCCAUGCUCGAAUGCCAGCAAUUUCUUGUCAUCG

AAGAGAAUAAGGUCCGCCAGUACGACUCCAUCCAGAAGCUGCUUAAUGAG

AGAUCAUUGUUCCGGCAGGCGAUUUCACCAUCCGAUAGGGUGAAACUUUU

UCCACACAGAAAUUCGUCGAAGUGCAAGUCCAAACCGCAGAUCGCGGCCU

UGAAAGAAGAGACUGAAGAAGAAGUUCAAGACACGCGUCUUUAA

5' and 3' UTR Sequences (SEQ ID NO: 9)
X=
GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACG (SEQ ID NO: 10)
Y=
CGGGUGGCAUCCCUGUGACCCCUCCCCAGUGCCUCUCCUGGCCCUGGAAG

UUGCCACUCCAGUGCCCACCAGCCUUGUCCUAAUAAAAUUAAGUUGCAUC

AAGCU

Lipid Nanoparticle Formulations

Ethanolic solution of mixture of lipids (cationic lipid, helper lipids, zwitterionic lipids, PEG lipids etc.) was prepared to the reported volume and heated to the selected temperature. Separately, an aqueous buffered solution (10 mM citrate/150 mM NaCl, pH 4.5) of mRNA was prepared from a 1 mg/mL stock and heated to the selected temperature for 5-10 minutes.

For small scale formulations, the lipid solution was injected rapidly into the aqueous mRNA solution using a syringe pump (3.71 mL/sec) and the resulting suspension was shaken to yield the lipid nanoparticles in 20% ethanol. The resulting nanoparticle suspension was dia-filtrated with 1×PBS (pH 7.4), concentrated and stored at 2-8° C.

Representative Example at 25° C.

Aliquots of 50 mg/mL ethanolic solutions of cKK-E12, DOPE, Chol and DMG-PEG2K were mixed and diluted with ethanol to 3 mL final volume. Separately, an aqueous buffered solution (10 mM citrate/150 mM NaCl, pH 4.5) of FFL mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=0.20 mg/mL FFL mRNA (encapsulated). $Z_{ave}$=91 nm PDI (0.16).

Formulation at 37° C.

Aliquots of 50 mg/mL ethanolic solutions of cKK-E12, DOPE, Chol and DMG-PEG2K were mixed and diluted with ethanol to 3 mL final volume. Separately, an aqueous buffered solution (10 mM citrate/150 mM NaCl, pH 4.5) of FIX mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=0.20 mg/mL FIX mRNA (encapsulated). $Z_{ave}$=64 nm; PDI (0.12).

Formulation at 65° C.

Aliquots of 50 mg/mL ethanolic solutions of cKK-E12, DOPE, Chol and DMG-PEG2K were mixed and diluted with ethanol to 3 mL final volume. Separately, an aqueous buffered solution (10 mM citrate/150 mM NaCl, pH 4.5) of FIX mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=0.20 mg/mL FIX mRNA (encapsulated). $Z_{ave}$=73 nm; PDI (0.13).

Effect of Temperature on the Nanoparticle Encapsulation Process

Both the ethanol lipid solution and the aqueous buffered solution of mRNA (10 mM citrate/150 mM NaCl, pH 4.5) were heated at different selected temperatures before the formulation process to determine the effect of temperature on the final yield and the encapsulation efficiency of the formulation.

The effect of temperature on the nanoparticle formulation process was evaluated for size, size dispersity, encapsulation efficiency and yield (or recovery). Exemplary data are shown in Table 1. As can be seen, an increase in temperature (e.g., above the ambient temperature) results in increased encapsulation efficiency and/or yield/recover, as well as reduced particle size and/or size dispersity.

TABLE 1

Effect of Temperature on Nanoparticle Formation and mRNA Encapsulation

| Formulation # | mRNA | Temperature | Size | PDI | Encapsulation | Recovery |
|---|---|---|---|---|---|---|
| Formulation process at ambient temperature (25° C.): | | | | | | |
| 1 | FFL | 25 | 91 | 0.16 | 71% | 30% |
| 2 | FFL | 25 | 88 | 0.14 | 76% | 33% |
| Formulation process at 37° C.: | | | | | | |
| 3 | FIX | 37 | 77 | 0.13 | 57% | 29% |
| 4 | FIX | 37 | 80 | 0.12 | 68% | 36% |
| 5 | FIX | 37 | 64 | 0.12 | 69% | 37% |
| 6 | FIX | 37 | 63 | 0.12 | 65% | 51% |
| Formulation process at 65° C.: | | | | | | |
| 7 | ASS1 | 65 | 86 | 0.12 | 85% | 64% |
| 8 | ASS1 | 65 | 84 | 0.11 | 96% | 98% |
| 9 | ASS1 | 65 | 81 | 0.16 | 86% | 64% |
| 10 | ASS1 | 65 | 84 | 0.11 | 96% | 98% |
| 11 | PAH | 65 | 79 | 0.12 | 82% | 77% |
| 12 | FIX | 65 | 73 | 0.13 | 81% | 77% |
| 13 | FIX | 65 | 79 | 0.14 | 92% | 82% |
| 14 | FIX | 65 | 85 | 0.13 | 95% | 70% |
| 15 | FFL | 65 | 68 | 0.10 | 92% | 78% |
| 16 | FFL | 65 | 83 | 0.12 | 91% | 77% |
| 17 | FFL | 65 | 80 | 0.11 | 91% | 75% |
| 18 | FFL | 65 | 83 | 0.11 | 88% | 72% |
| 19 | FFL | 65 | 80 | 0.16 | 90% | 75% |
| 20 | FFL | 65 | 78 | 0.11 | 81% | 77% |
| 21 | FFL | 65 | 86 | 0.12 | 82% | 75% |

Example 2

Scaled-Up Formulation Process

This example illustrates an exemplary scaled-up formulation process for encapsulating mRNA at an increased temperature.

An exemplary scaled-up formulation process is shown in FIG. 1. Ismatec programmable digital drive pumps (Cole Parmer Model # CP 78008-10) were used. Micropump A-mount Suction Shoe Pump Head 316 SS body/graphite gears/PTFE seals, 0.084 mL/rev, w/out internal bypass (Cole Parmer Model #07002-27) and Pharma Pure Tubing Size 14, 0.06" ID, ¹⁄₁₆" (Spectrum labs Part # ACTU-P14-25N) were used.

Nanoparticle formulation and encapsulation of mRNA is prepared by mixing an ethanol lipid solution with mRNA in citrate buffer (10 mM citrate buffer, 150 mM NaCl, pH 4.5) using a 'T' junction (or "Y" junction). Exemplary flow rates for the mRNA in citrate buffer and lipids in ethanol solution are 200 mL/minute and 50 mL/minute respectively. During this process, both pumps are started simultaneously. Both the starting and the end fractions of the formulations are discarded, only the intermediate formulation is collected. Accurate flow rates and pulse less flow are two important parameters of this process.

Purification and Buffer Exchange

Figure 2:
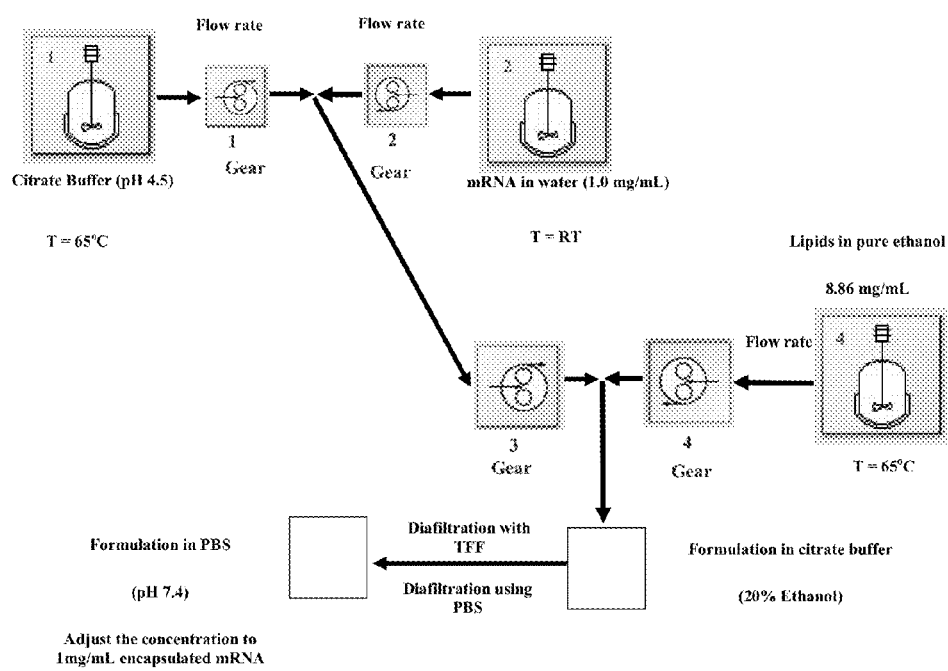
FIG. 2: depicts an exemplary purification and buffer exchange system for lipid nanoparticles.

Purification and buffer exchange of the formulation from the above step is performed with KrosFlo® Research IIi Tangential Flow Filtration system from Spectrum labs using the modified polyethersulfone hollow fiber filter modules. Buffer exchange is performed with 6× volumes of sterile PBS (pH 7.4) in a continuous diafiltration form. See FIG. 2. Formulation is analyzed for Size (PDI) and encapsulation (yield). Exemplary data is presented in Table 2.

TABLE 2

Examples of scaled-up formulation

| Formulation | Batch Size (mg) | N/P | mRNA | Size (nm) | PDI | Encapsulation |
|---|---|---|---|---|---|---|
| 22 | 5 | 4 | ASS1 | 59 | 0.09 | 88% |
| 23 | 5 | 4 | ASS1 | 60 | 0.12 | 81% |
| 24 | 5 | 4 | ASS1 | 59 | 0.11 | 92% |
| 25 | 5 | 4 | ASS1 | 62 | 0.12 | 91% |
| 26 | 5 | 4 | ASS1 | 59 | 0.11 | 89% |
| 27 | 5 | 4 | ASS1 | 62 | 0.07 | 97% |
| 28 | 5 | 4 | ASS1 | 57 | 0.12 | 91% |
| 29 | 5 | 4 | ASS1 | 62 | 0.07 | 97% |
| 30 | 5 | 4 | ASS1 | 67 | 0.12 | 88% |
| 31 | 5 | 4 | ASS1 | 60 | 0.15 | 82% |
| 32 | 5 | 4 | ASS1 | 75 | 0.09 | 92% |
| 33 | 5 | 4 | ASS1 | 67 | 0.12 | 91% |
| 34 | 5 | 4 | ASS1 | 71 | 0.13 | 92% |
| 35 | 5 | 4 | ASS1 | 69 | 0.11 | 92% |
| 36 | 5 | 4 | ASS1 | 66 | 0.13 | 94% |
| 37 | 5 | 4 | ASS1 | 72 | 0.11 | 94% |
| 38 | 5 | 4 | ASS1 | 82 | 0.13 | 96% |
| 39 | 5 | 4 | ASS1 | 62 | 0.12 | 90% |
| 40 | 5 | 4 | ASS1 | 60 | 0.11 | 86% |
| 41 | 5 | 4 | ASS1 | 67 | 0.15 | 91% |
| 42 | 5 | 4 | ASS1 | 69 | 0.14 | 94% |
| 43 | 5 | 4 | ASS1 | 65 | 0.16 | 90% |
| 44 | 5 | 4 | ASS1 | 63 | 0.12 | 89% |
| 45 | 5 | 4 | ASS1 | 65 | 0.08 | 86% |
| 46 | 5 | 4 | GLA | 62 | 0.11 | 95% |
| 47 | 5 | 4 | GLA | 57 | 0.16 | 89% |
| 48 | 5 | 4 | GLA | 54 | 0.08 | 95% |
| 49 | 5 | 4 | GLA | 62 | 0.12 | 88% |
| 50 | 5 | 2 | SMN | 61 | 0.14 | 81% |
| 51 | 5 | 4 | 25% s2U, 25% 5 mC CFTR | 60 | 0.13 | 96% |
| 52 | 20 | 2 | ASS1 | 72 | 0.10 | 90% |
| 53 | 20 | 4 | ASS1 | 75 | 0.12 | 92% |
| 54 | 20 | 4 | ASS1 | 81 | 0.11 | 82% |
| 55 | 20 | 6 | FFluc | 82 | 0.11 | 94% |
| 56 | 20 | 4 | FFLuc | 78 | 0.11 | 94% |
| 57 | 20 | 4 | CFTR | 80 | 0.12 | 98% |
| 58 | 30 | 4 | CFTR | 75 | 0.12 | 85% |
| 59 | 50 | 4 | CFTR | 69 | 0.17 | 92% |
| 60 | 50 | 2 | ASS1 | 73 | 0.15 | 82% |
| 61 | 60 | 4 | ASS1 | 71 | 0.13 | 95% |
| 62 | 300 | 2 | ASS1 | 59 | 0.18 | 95% |
| 63 | 300 | 4 | ASS1 | 64 | 0.11 | 96% |
| 64 | 1000 | 2 | ASS1 | 51 | 0.18 | 89% |
| 65 | 1000 | 4 | ASS1 | 61 | 0.19 | 91% |
| 66 | 1000 | 2 | ASS1 | 56 | 0.18 | 81% |
| 67 | 1000 | 4 | ASS1 | 71 | 0.08 | 92% |
| 68 | 1000 | 2 | ASS1 | 51 | 0.12 | 90% |
| 69 | 1000 | 4 | ASS1 | 73 | 0.13 | 89% |
| AVERAGE | | | | 65.8 | 0.12 | 91% |

Using this process, very narrow particle size range is achieved as well as high encapsulation efficiency (e.g., >90% average).

Figure 3:
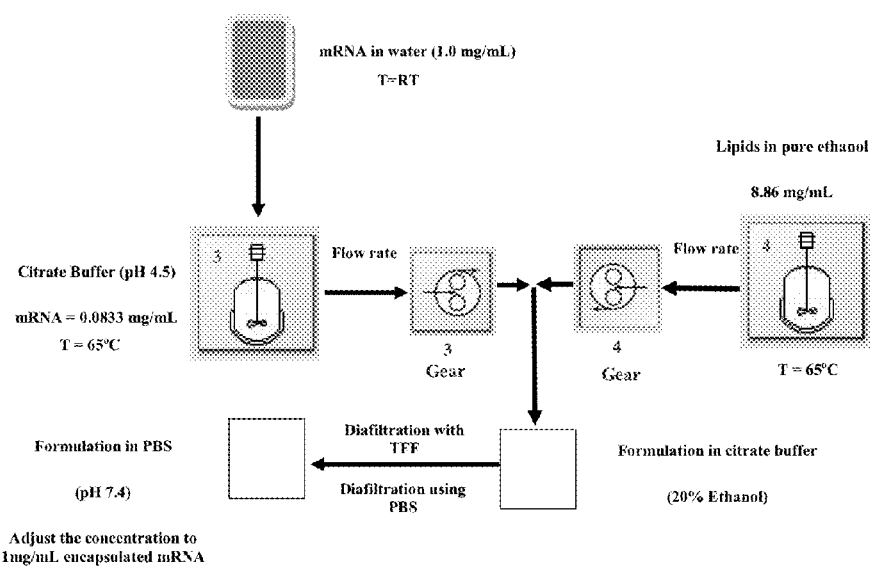
FIG. 3: depicts a schematic of an exemplary scaled-up lipid nanoparticle encapsulated mRNA formulation process with peristaltic pumps.
Figure 4:
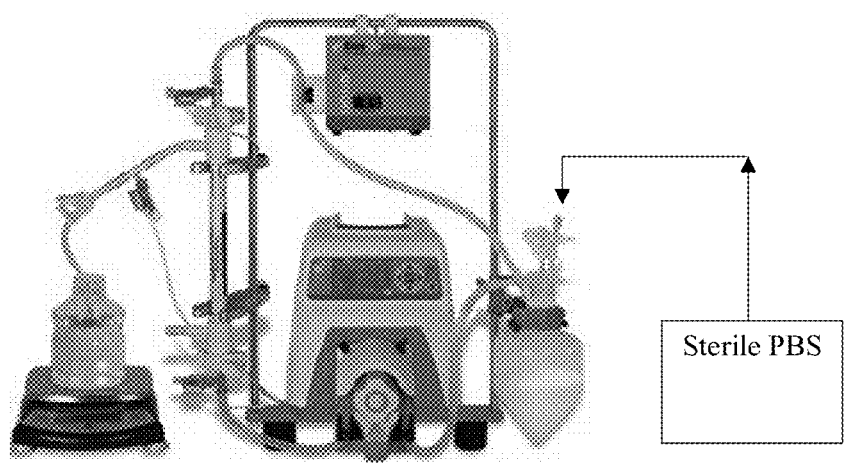
FIG. 4: depicts an alternative exemplary tangential flow filtration system for purification and buffer exchange.

To test the importance of pulse-less homogeneous flow, peristaltic pumps that have some degree of pulsating flow were used for the formulation process. See FIG. 3. mRNA in citrate buffer and lipids in pure ethanol were mixed at flow rate of 200 mL/minute and 50 mL/minute respectively. Exemplary results were shown in Table 3. As can be seen, the use of peristaltic pumps within this process results in the formulation of nanoparticles with larger size. This is likely due to non-homogeneous mixing due to pulsating flow.

TABLE 3

Examples of formulations with peristaltic pumps

| Formulation # | mRNA | Size (nm) | PDI |
|---|---|---|---|
| 70 | CFTR | 112 | 0.19 |
| 71 | CFTR | 116 | 0.17 |
| 72 | FFL | 128 | 0.14 |
| 73 | FFL | 134 | 0.16 |

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A process of encapsulating messenger RNA (mRNA) in lipid nanoparticles comprising steps of:
   generating an mRNA solution by mixing a citrate buffer at a flow rate of about 220 ml/minute to about 6000 ml/minute with an mRNA stock solution; and
   mixing the mRNA solution and a lipid solution by a pulse-less flow pump, wherein the mRNA solution and/or the lipid solution are at a pre-determined temperature greater than ambient temperature.

2. The process of claim 1, wherein the pre-determined temperature is about 65° C.

3. The process of claim 1, wherein the mRNA solution is mixed at a flow rate of about 200 ml/minute.

4. The process of claim 1, wherein the lipid solution is mixed at a flow rate of about 50 ml/minute.

5. The process of claim 1, wherein the mRNA stock solution comprises the mRNA at a concentration at or greater than 1 mg/ml.

6. A process of encapsulating messenger RNA (mRNA) in lipid nanoparticles comprising steps of:
   generating an mRNA solution by mixing an mRNA stock solution at a flow rate of about 20 ml/minute to about 600 ml/minute with a citrate buffer;
   mixing the mRNA solution and a lipid solution by a pulse-less flow pump, wherein the mRNA solution and/or the lipid solution are at a pre-determined temperature greater than ambient temperature.

7. The process of claim 1, wherein the lipid solution comprises one or more cationic lipids, one or more helper lipids, one or more cholesterol-based lipids and PEG lipids in ethanol.

8. The process of claim 1, wherein the mRNA solution and the lipid solution are mixed into a 20% ethanol, resulting in a suspension of lipid nanoparticles.

9. The process of claim 8, wherein the lipid nanoparticles are further purified by Tangential Flow Filtration.

10. The process of claim 6, wherein the pre-determined temperature is about 65° C.

11. The process of claim 6, wherein the mRNA solution is mixed at a flow rate of about 200 ml/minute.

12. The process of claim 6, wherein the lipid solution is mixed at a flow rate of about 50 ml/minute.

13. The process of claim 6, wherein the mRNA stock solution comprises the mRNA at a concentration at or greater than 1 mg/ml.

14. The process of claim 6, wherein the lipid solution comprises one or more cationic lipids, one or more helper lipids, one or more cholesterol-based lipids and PEG lipids in ethanol.

15. The process of claim 6, wherein the mRNA solution and the lipid solution are mixed into a 20% ethanol, resulting in a suspension of lipid nanoparticles.

16. The process of claim 15, wherein the lipid nanoparticles are further purified by Tangential Flow Filtration.

* * * * *